United States Patent [19]

Beaver et al.

[11] Patent Number: 4,469,601
[45] Date of Patent: Sep. 4, 1984

[54] SYSTEM AND APPARATUS FOR MULTI-DIMENSIONAL REAL-TIME CHROMATOGRAPHY

[75] Inventors: Lois A. Beaver, Rockville, Md.; Georges A. Guiochon, Paris, France

[73] Assignee: Varex Corporation, Rockville, Md.

[21] Appl. No.: 415,760

[22] Filed: Sep. 7, 1982

Related U.S. Application Data

[63] Continuation-in-part of Ser. No. 244,743, Mar. 17, 1981, abandoned.

[51] Int. Cl.³ .............................................. B01D 15/08
[52] U.S. Cl. .................................. 210/658; 210/198.3
[58] Field of Search ................... 210/658, 198.2, 198.3

[56] References Cited

U.S. PATENT DOCUMENTS

| | | | |
|---|---|---|---|
| 3,229,505 | 1/1966 | Sanford et al. | 210/198.3 |
| 3,522,792 | 8/1970 | Delfel | 118/415 |
| 3,591,805 | 7/1971 | Schoeffel | 210/198.3 |
| 3,598,995 | 8/1971 | Inoue | 210/198.3 |
| 3,635,345 | 1/1972 | Rodder | 210/198.2 |
| 3,759,773 | 9/1973 | Dwyer et al. | 210/198.3 |
| 3,928,203 | 12/1975 | Kremer | 210/198.3 |
| 4,065,384 | 12/1977 | Pandey et al. | 210/658 |
| 4,261,835 | 4/1981 | Creeger | 210/198.3 |
| 4,313,906 | 2/1982 | Filipi et al. | 422/69 |
| 4,346,001 | 8/1982 | Tyihak et al. | 210/198.3 |

FOREIGN PATENT DOCUMENTS

| | | | |
|---|---|---|---|
| 1498678 | 5/1961 | Fed. Rep. of Germany | 421 |
| 2237790 | 5/1973 | Fed. Rep. of Germany | 210/198.3 |
| 173749 | 11/1979 | Hungary . | |
| 475679 | 2/1972 | Japan | 210/198.3 |
| 442804 | 1/1968 | Switzerland | 421 |
| 1213445 | 11/1970 | United Kingdom | 210/198.3 |
| 439693 | 7/1972 | U.S.S.R. | 210/198.3 |

OTHER PUBLICATIONS

The Relationship Between One-Dimensional and Two-Dimensional Separation Processes, by Wankat, in AICHE Journal, (vol. 23, No. 6), 11/1977, pp. 859–867.

J. Taylor, N. L. Anderson, B. P. Coulter, A. E. Scandora, Jr., and N. G. Anderson, "Estimation of Two Dimensional Electrophoretic Spot Intensities and Positions by Modeling", *Electrophoresis*, (1979), © 1980.

P. F. Lemkin and L. E. Lipkin, "Gellab": A Computer System for 2-D Gel Electrophoresis Analysis, 1: Segmentation of Spots and System Preliminaries, *Computers and Biomedical Research* 14, 272–297, (1981).

(List continued on next page.)

[57] ABSTRACT

A column and detector are disclosed for two-dimensional column chromatography of a sample, in which the sample is injected close to a corner of a thin parallelepipedal column through which percolates a first solvent pumped at a controlled velocity. After a convenient time this flow is stopped and a stream of a second solvent is pumped at a controlled velocity in the perpendicular direction. Elution of the separated components is performed, the stream exiting from the column flows over a detector which monitors its composition at a large number of points, along the exit edge allowing the derivation of a two-dimensional chromatogram. The chromatographic bed can be homogeneous or made of a first portion including a first composition suitable to perform column chromatography in the first direction of the column and a second portion including a second composition suitable to perform column chromatography in a second direction of the column, wherein both compositions are selected from compositions available for column chromatography. A method for making a column and detector for three-dimensional chromatography is also disclosed. Methods for using such columns and detectors, over-pressure development of conventionally read two-dimensional thin column chromatograms, use of the thin-layer column as a multi-column chromatograph, injection of unknowns into the flowing solvent, optimum flow rates, and a special cuvette plate and associated apparatus for performing the methods are also disclosed.

36 Claims, 21 Drawing Figures

OTHER PUBLICATIONS

N. L. Anderson, J. Taylor, A. E. Scandora, B. P. Coulter, and N. G. Anderson, "The TYCHO System for Computer Analysis of Two-Dimensional Gel Electrophoresis Patterns", *Clinical Chemistry*, 27/11, 1807-1820, (1981).

E. P. Lester, P. F. Lemkin and L. E. Lipkin, "New Dimensions in Protein Analysis", Two-Dimensional Gel Techniques are coming of Age as Image Processingis Applied to Computer Analysis of the Data, *Analytical Chemistry* 53, 390A, (1981).

E. Tyihak, E. Mincsovics and J. Kalasz, "New Planar Liquid Chromotographic Technique: Overpressure Thin-Layer Chromatography", *Journal of Chromatography*, 174, pp. 75-81, (1979).

E. Tyihak, E. Mincsovics, H. Kalasz and J. Nagy, "Optimization of Operating Parameters in Overpressured Thin-Layer Chromatography", *Journal of Chromatography*, 211, pp. 45-51, (1981).

E. Mincsovics, E. Tyihak and H. Kalasz, "Resolution and Retention Behavior of Some Dyes in Overpressured Thin-Layer Chromatography", *Journal of Chromatography*, 191, pp. 293-300, 1980.

H. Issaq, "Two-Phase Thin-Layer Chromatography", *Journal of Liquid Chromatography*, 3(6), pp. 841-844, 1980.

H. Kalasz, J. Nagy, E. Mincsovics and E. Tyihak, "Circular-Development with Overpressured Thin-Layer Chromatography", *Journal of Liquid Chromatography, 3(6), pp. 845-855, 1980.*

E. Soczewinski, "Simple Device for Continuous Thin-Layer Chromatography", *Journal of Chromatography*, 138, pp. 443-445, 1977.

T. Mezzetti, M. Ghebregziabhier, S. Rufini, G. Ciuffini and M. Lato, "Coupled Layers: A New Technique for the Two-Dimensional Thin-Layer Chromatography of Carbohydrates", *Journal of Chromatography*, 74, pp. 273-296, 1972.

Sales Literature: Chrompres "Overpressured Thin Layer Chromatography A New Planar Liquid Chromatorgraphic System", Type OE-306, pp. 1-3, and one page photographs.

Sales Literature: TELECHROM-S OE 976, "The New High-Speed Video-Densitometer", 3 pages.

*Primary Examiner*—John Adee
*Attorney, Agent, or Firm*—F. Eugene Davis, IV

SYSTEM AND APPARATUS FOR MULTI-DIMENSIONAL REAL-TIME CHROMATOGRAPHY

RELATED APPLICATION

This application is a continuation-in-part of our prior U.S. patent application, Ser. No. 244,743, filed Mar. 17, 1981, entitled SYSTEM AND APPARATUS FOR MULTI-DIMENSIONAL REAL-TIME CHROMATOGRAPHY now abandoned.

TECHNICAL FIELD

This application relates to multi-dimensional multi-phase chromatography employing real-time detection. More particularly it relates to such chromatography employing fluid separation of an unknown's constituents, particularly thin layer chromatography, with at least the second dimensional, second phase, separation performed by continuous overpressured thin-layer chromatography with novel real-time multiple linear array detection means. The unknown is injected into the flowing stream.

A three dimensional scheme according to the invention is also disclosed.

Use of the two-dimensional system employing real-time quasi-real-time detection permnits separation of as many as five hundred to one thousand components of an unknown depending on the size of the chromatographic plate and the use of data processing means to process the data and present it in convenient form.

BACKGROUND ART

The separation of complex mixtures is a task of major importance for the analyst and there are several fields now where considerable effort is made solving that kind of problems, in biochemical, clinical, environmental, food and petroleum chemistry especially.

Chromatography is by nature the most efficient separation method the analyst can use and is the backbone of all separation schemes devised. The supremacy of chromatography is a consequence of its important separation power and of the wide range of retention mechanisms which are available, most of them offering tunable selectivity by adjusting the composition of the mobile phase. It is rare, however, that the separation of a complex mixtures can be solved using one chromatographic column, either in isochratic or graident conditions.

The separation power of a chromatographic column is best expressed by its peak capacity, the number of peaks with resolution unity which are eluted between $k'=0$ and a final value, usually 6.4 but rarely exceeding 10. The peak capacity of a conventional packed LC column can hardly exceed a few hundreds: a hundred thousand plate column which is already a rarity, has a peak capacity between 160 ($k'=6.4$) and 240 ($k'=20$). It has been shown that assuming a Poisson distribution of the $k'$ of the compounds of the analyzed mixture in the range of $k'$ recorded, it cannot be used to separate much more than about 150 peaks and even for less complex mixtures a number of peaks will be multiplets, i.e. the corresponding compounds will interfere. Previous work has shown that there is little hope to increase much the peak capacity available beyond several hundreds, even by accepting very long analysis times and resorting to capillary columns of very small diameter (less than 5 micrometers) and meeting the exacting specifications their successful use demands.

Accordingly, the analysis of complex mixtures is usually attempted by combinations of selective extractions and chromatographic separations. This is time consuming, tedious, and costly because of all the additional efforts to avoid the soures of errors due to contamination and losses. So called multi-dimensional chromatography separates on a second column on fraction purified on a first column, but cannot be applied to the entire sample. An analytical scheme using several retention mechanisms integrated into a continuous series of operations applied to a sample in one single equipment would solve all these problems and simplify considerably the data handling, since all quantitative results would apply to the same sample.

Two dimension thin layer chromatography $(TLC)^2$ operates on such a principle. In this method a plate is covered with silica gel. In single phase chromatography, an unknown is placed on the plate and the plate is placed in a beaker containing enough solvent to wet the lower edge of the plate. As the solvent climbs up the silica gel layer on the plate by capillary attraction, it moves the sample along with it. However, the different constituents of the sample having different affinities for the silica gel, are separated. The development is stopped when the first constituent reaches the top of the plate. The plate is dried. The constituents can be detected as spots at different positions on the slica gel. The silica gel may also be treated in various ways: e.g., so that it is polar, in which case non-polar solvents may be utilized; or vice versa; or it may be coated with certain molecules having specific affinities for the suspected unknowns. Thus the unknowns may be separated by their polar properties, by their molecular weights or by certain chemical affinities.

The first separation using $(TLC)^2$ was published 40 years ago by Consden, Gordon and Martin. They used a 55×45 cm sheet of Whatman paper to separate alpha-amino acids. The first development was made with a mixture of collidine and water. It lasted 72 hours. After drying, a second development using phenol/water in an atmosphere containing coal gas and ammonia was carried out for another 48 hours. Detection was based on the ninhydrine reaction. At least 15 of the 22 proteinic amino acids were separated. Sample size was 200 micrograms of protein hydrolyzate and sensitivity 1 microgram. The spot capacity of the paper sheet can be estimated at slightly over 100.

In two-dimensional thin layer chromatography $(TLC)^2$ the chromatographic plate is coated in a strip along one edge with one form of treated or untreated silica gel and along the rest of the plate with a different form of treated or untreated silica gel. The plate is first developed along the strip by placing an edge perpendicular thereto into a beaker of appropriate solvent to separate the unknown into a linear array of constituents. After drying the plate is placed into another beaker of another solvent along the edge parallel to the linear array of constituents and they are developed up the plate to form a planar array of sub-constituents.

After drying, in order to analyze the plate, these sub-constituents must be detected and their position on the plate, and density, measured either by eye or by automatic means. Such means are expensive, and due to the spread out nature of the spots of the sub-constituents on the plate, are not very accurate.

Since there is no control of the speed of the solvent moving up the plate, reproduceability is not good. This greatly limits the efficacy of this system of analysis. In terms of quantitative analysis (derived from density measurements) results better than 10 to 20% accuracy are very difficult to obtain.

Furthermore, the development of such thin-layer chromatographic plates is time consuming, taking up to several hours in each direction. Recently however pressurized thin-layer chromatography has come into use to try to avoid this time difficulty. In this system the solvent is forced through the thin layer of a retention medium by placing a cover plate over the thin layer of retention medium. This system has increased the speed of development.

(TLC)[2] has developed slowly over the years. The number of publications where this technique is described or used exceeds 200, which is neither negligible nor very important. The major technological advances since the original paper have stemmed out from the progress in thin-layer chromatography (TLC) technology. The major drawbacks of the technique are (1) the difficulties in making plates with a lateral strip of a stationary phase different from the one used for the main part of the plate which makes difficult the use of retention mechanisms based on different stationary phases; (2) the cross-contamination between the two developments, i.e. the retention pattern obtained during the second development is influenced by evaporation residuals of the first solvent and is different from the retention pattern obtained directly with the second solvent on the same stationary phase; (3) the quadratic law of solvent front migration and the unfavorable relationship between the particle size and the kinetic coefficient of the plate, which prevents from using fine particles with moderately large plates and achieving large bed efficiency; (4) the sample solution is applied on the dry bed and the solvent dried out; this promotes strong selective or irreversible adsorption, clogs adsorbent particles with viscous or solid material slow to dissolve in the mobile phase, resulting in strong tailing; (5) the near impossibility to achieve directly quantitative analysis.

This last drawback is probably the most bsic and the most serious. It is already difficult to scan a conventional TLC plate. The signal does not follow the Behr law but the more complex Kubelka-Munk function. Sensitivity is moderate and the size of the scanner light beam is as large or larger than one spot standard deviation when it should be 5 times smaller. It cannot be reduced in size, however, because the noise due to the granular appearance of the surface would become too large. The compromise between sensitivity and contribution to band broadening cannot be made satisfactory. For this reason high resolution scanners such as those used for two-dimensional gel electrophoresis with a spatial resolution of 0.1 mm cannot be used with success in (TLC)[2] and a Vidicon Camera needs extensive digital filtering of the data, with all the difficulties associated with it.

To solve most of these problems we combine (TLC)[2] with over pressured development. Over pressure development was suggested by Tyihak et al for conventional thin layer chromatography (TLC). A plastic membrane is applied under pressure against the surface of the TLC plate, effectively sealing chromatographic bed between it and the plate support. The solvent can be pumped through the bed at the required velocity as long as the corresponding inlet pressure is smaller than the pressure applying the membrane. Originally invented for centrifugal TLC this technique has been extended to conventional linear TLC through the use of a distributor. This permits solving the third of the five problems discussed above.

More recently a system quite similar to those previously mentioned has been designed with the aim of achieving conditions analogous to those prevailing in high pressure liquid chromatography (HPLC) so that retention data measured by TLC can be used without correction in column chromatography. A TLC plate is protectedp by a shield which does not touch it; the end of the TLC plate protrudes out of this enclosure and is swept by a warm gas stream which vaporizes the solvent when it exits from under the shield. The plate is horizontal and the solvent phase is fed to it through a capillary siphon and a distributor. The relative positions of the plate, the tip of the siphon and the solvent tank prevents flooding the plate while supplying a sufficient amount of solvent to keep it normally wet. In these conditions a steady-state is achieved and constant speed of the mobile phase is obtained. It is not possible to adjust it, however. The speed is approximately equal to what would be derived from the quadratic law, using for plate length the distance between the distributor and the front of mobile phase resulting from its vaporization. The sample is injected with a syringe, downstream of the distributor, after the steady flow of solvent is achieved. This eliminates the difficulties associated with demixing of solvent mixtures in conventional TLC.

Excellent analytical results have been obtained with this system. Retention data compares very closely to those measured in column chromatography. Spot shape is considerably improved with drastic reduction of the trailing due to irreversible sorption by the dry adsorbent or slow dissolution of concentrated samples. A slightly modified version of this instruction has also been used to provide an elegant pilot technique for the optimization of preparative column chromatography.

The method is very simple, provides reliable results, permits considerable solvent savings and is certainly a major advance in the art of TLC, but unfortunately it has not yet received the audience it deserves. Its drawbacks are the impossibility of adjusting the solvent velocity except by changing particle size or development length, i.e. separation power, and the lack of on-line detection.

Another system is identical to the above one as far as the chromatographic part is concerned, except for the use of a wick instead of a siphon to feed the plate with the solvent. There is a signficant addition to the earlier devices, however, in the use of a UV photometer to detect the spots before they reach the exit wick. Thus a chromatogram is obtained similar to those given by an HPLC equipment, with little advantage beyond simplicity but the marked drawbacks of a flow velocity which cannot be adjusted, of a very short optical path length and a spot detection based on UV absorption carried out on a porous diffusive medium. For these reasons we do not believe that this principle is more expedient than HPLC for routine analysis.

The data published show that the resolution obtained with the new system is comparable to that achieved using the same TLC plate in a conventional manner. On the other hand the reproducibility of retention times is markedly improved, as could reasonably be expected when a method using a steady state stream, like TCC, is compared to a method using a transient-state stream like TLC, because of the complexities of the phenomena involved in TLC flow.

A more sophisticated chromatographic system has been described by Tyihak and his associates. The basic principle is to cover the sorbent layer of a TLC system by a plastic membrane applied under an external pressure. The membrane fills the irregularities of the smooth layer surface and together with the layer support makes a porous sandwich analogous to a column through which solvent can be forced under pressure. With this technique called over-pressure TLC which is indeed an actual kind of column chromatography using a column of non-conventional cros section, the velocity of the mobile phase can be adjusted at will, by setting the solvent inlet pressure at the required value, as long as it is smaller than the external pressure applying the membrane on the sorbent layer. Originally the method was limited to circular, centrifugal developement for obvious reasons of simplicity in the design, using a circular chamber with a solvent inlet at the cente,r but in a more advanced system the use of a distributor permits parallel development of a number of samples as in conventional TLC.

Experimental data demonstrate that the distance travelled by the solvent is proportional to time and not given by the quadratic law anymore, that the flow velocity of the solvent can be adjusted independently of development distance and particule size, that the retention is highly reproducible and not significantly changed by the development distance, which is not true in conventional TLC, and that the plate height does not depend anymore on the migration distance since the solvent velocity is kept constant. We note in passing that the plate height achieved, which may not be the minimum, is approximately 15 micrometers with HPTLC particles and 33 micrometers with TLC particules leading to a value of the reduced plate height of about 2–2.5, in agreement with out independent estimates of the plate performances. The solvent velocity is 0.25 mm/second in both cases, corresponding to a reduced velocity of about 1.8 in the first case and 3.5 in the second. These results are quite similar to those obtained in column chromatography. As a consequence the separation number obtained increases monotonically with solvent migration distance instead of going through a maximum smaller than 20 as it does in TLC. Needless to say, excellent analytical results are obtained.

This excellent chromatographic bed design is very close to a column with a thin rectangular profile. Its major drawback is that it is operated by starting with a dry layer, placing the samples as inconventional TLC and after pressurizing the membrane, flowing the solvent stream into the dry layer. There is no need of operating this way, although it saves solvent. Better results, especially for weakly retained compounds may be obtained using on-line injection after a steady solvent stream is established. Furthermore, this system suffers from a lack of on-line detection.

Finally, several groups have developed during these last few years a scheme to separate over a thousand different proteins and analyze them quantitatively using bi-dimensional electrophoresis. Although the separation mechanism is different from chromatography and the technological problems involved are not related, there is obviously a close relationship between the principles of the two techniques, $(TCC)^2$ and $(electrophoresis)^2$. Indeed, electrophoresis can be used for each separation mechanisms but the last in $(CC)^2$, $(CC)^3$ or $(TCC)^2$. The software used for data acquisition and handling is also quite similar.

DISCLOSURE OF THE INVENTION

In our invention a column which, for sake of convenience will be assmed to be square but does not need to be, is packed either entirely or almost completely with a stationary phase of conventional retention media used in high performance liquid chromatography (HPLC). This may be, for example, plain silica, reversed phase material, size exclusion material, ion exchange resin, etc. In some cases a narrow strip along one side of the column is packed with a different material of identical size. A first solvent is pumped in the direction parallel to that strip; after a steady stream is achieved the sample is injected near the far corner of the column and one column volume is pumped or more if the first compounds of interest are retained on this first chromatographic separation. After the flow of this first solvent is stopped, a second solvent is pumped in the perpendicular direction and the sample components are eluted out of the column and carried through a detector unit which is the equivalent of a large array of conventional HPLC detectors parallel to the exit edge of the plate. The separated peaks can be reconstructed from the detector signals as a three dimensional plot of concentration versus time and abscissa along the exit edge.

The two chromatographic systems must fulfill two conditions: (1) they must give retention patterns widely different for the components of the analyzed mixture, e.g. one separates by molecular size, the other by polarity and/or polarizability; (2) they must be compatible in the sense that the first solvent should not destroy the second adsorbent and should be either miscible with the second solvent or easy to get rid of. This can be achieved by pumping an inert gas in the second direction or a third solvent, miscible to both the first and second and of small elution strength in the second direction.

This method which we call two-dimensional column chromatography $(CC)^2$ is a method which combines the advantages of column chromatography (constant, adjustable flow velocity, excellent efficiency, on-line detection on solution) and two-dimensional thin-layer chromatography (successive developments in two perpendicular directions, using two different retention mechanisms).

By merely keeping constant the solvent flow velocity during the development of a TLC plte, a considerable increase in the spot capacity can be achieved, since plate length and particule size can be selected now without any prejudicial influence on the solvent velocity which can be kept constant at the value considered as optimum by the analyst.

Calculations show that $(CC)^2$ can generate peak capacities well in excess of 500, up to several thousands, and that the specifications for the equipment are not drastic. A $10 \times 10$ cm column would be 1 mm thick, be well packed with 10 micrometer particles and be operated at a reduced velocity of 10. Such a packing could be expected to be very homogeneous $(A=0.7)$ and the reduced plate height would be 1.95. The expected spot capacity is 900, while the pressure drop for a compound with $D=5 \times 10^{-6}$ cm$^2$/s ($u=0.05$ cm/s) and a solvent with viscosity 1 cP is only 5 atm (flow rate 3 cm$^3$/min). The sample spot should be about 1 mm diameter or less.

In the system and apparatus described, an unknown mixture is placed at one end of a strip of material utilizing a first retention mechanism and an appropriate solvent is forced through the strip which is placed under a cover plate so that the solvent is eluted out the other end of the strip until a first constituent reaches the end of the strip at which time the elution is stopped. Adjacent to the first strip is a two-dimensional thin layer of material having a second retention mechanism. The layer and strip which may be on a single plate are then placed under a cover plate and the appropriate solvent for the second retention mechanism is forced across the strip orthogonal to the array of constituents and eluted out the other side of the plate opposite the strip. A vacuum device may be attached to the eluting edge to aid in this process. The plate is either supplied with a transparent slit at the edge of the plate or a transparent slit is provided adjacent the edge through which the solvent elutes in a laminar fashion. In one embodiment of the invention the slit is illuminated with ultraviolet light and a multi-photo diode linear array on the other side of the slit detects the ultraviolet light. When a sub-constituent passes through the slit, it is detected by the diode array. The time and position of the detection is an indication of the nature of the sub-constituent and the amount of absorption is an indication of the quantity of the sub-constituent. The output from the diode array may be recorded on magnetic tape and processed by a computer in order to provide a pseudo-three-dimensional plot or cathode ray display in the form of mountain peaks of the sub-constituents arrayed on a two-dimensional flat plate. The position of the peaks indicates the nature of the constituent, and the volume of the mountain the quantity of the constituent. Alternatively, the computer may be programmed to provide a list of the components and their quantities. Alternatively, a fast computer with a large memory can be used to process the output of the detector in real-time.

Thus, we use a two-dimensional column, eluted successively along the two perpendicular directions. The column is identical to the thin, two-dimensional layer used in two-dimensional TLC $(TLC)^2$ but is used differently. The sample is introduced in a corner of the plate as in $TLC^2$ but instead of relaying on capillarity and surface tension of solvents to develop the chromatogram, the layer is pressurized and a conventional HPLC pump is used to force a stream of solvent across the column, parallel to one of its dimensions first, until the less retained compounds of interest migrate close to the plate edge opposite to the sample introduction (see FIG. 1). This first, forced development achieved, a second solvent stream is pumped in the perpendicular direction. It is possible to stop this second development when the fastest compunds of interest reach the opposite edge. The two-dimensional chromatogram is then read conventionally. Then the only advantage over $(TLC)^2$ is that the flow velocity of both solvents is controlled during the entire process, permitting the choice of an optimum velocity, irrespective of the particule size of the stationary phase and of the viscosity, surface tension or contact angle of the mobile phase. This velocity can be maintained constant whatever the column length and the sample can be applied after an equilibrium is reached between the first solvent and the adsorbent, thus offering more reproducible retention data. We call this procedure two-dimensional thin column chromatography or $(TCC)^2$ to distinguish it from $(TLC)^2$.

Another, more powerful, aspect of our invention is to elute the compounds out of the bed of stationary phase and detect them on-line, as in HPLC. The cross section of the fluid at the column outlet is a thin, long rectangle. This stream flows over a diode array aligned along the column exit slit and is irradiated by an appropriate UV light beam. Alternatively a flying spot or a Vidicon can be used. Thus the local changes of absorption of the mobile phase when spots are eluted can be monitored and recorded using the signals collected from the hundreds of pixels of the diode array. An x, t, c two-dimension chromatogram can thus be obtained. It takes more time to record it than to develop a $(TCC)^2$ chromatogram but quantitative data are available right away, whereas the $TCC)^2$ chromatogram remains to be scanned. We call this procedure two-dimensional column chromatography or $(CC)^2$.

Obviously the same principles can be used to carry out three-dimensional separations using $(CC)^3$.

Although this separation scheme is new, the idea to control and adjust the flow velocity in TLC is not and definitive progress along this line have been made recently. Brenner and Neiderweiser were probably the first to suggest the use of a simple device that forces solvent to run over, thus providing a steady mobile phase velocity for the development of a thin-layer plate. They were interested merely in overdevelopment, however, as were Hara and Mibe and many others like Snyder.

The advantages of having a steady stream of solvent flowing along the thin layer bed are essentially the measurement of more reproducible retention data, of retention data which match closely those obtained in column chromatography, the use of a constant velocity and constant plate height for a given compound during the development, possibility to optimize analysis time and separation by adjusting separately the development length and the particle size, the possibility to detect spots during their migration by light absorption or reflexion. If in addition the thin layer bed is enclosed and the solvent can be forced through it, two additional advantages are the possibility to adjust the flow velocity to an optimum value independently of the development length and particle size and on-line detection on the bulk solvent down stream the column exit, without interference from the diffusive stationary phase medium.

In a three-dimensional form of the apparatus, the second dimensional development is ceased when the first subconstituent reaches the edge of the plate. The plate is permeable and when dried, is placed against a cube of a material having a third retention mechanism and a third solvent is forced through the plate and through the cube. A vaccuum device at the opposite side of the cube aids in the elution. Detection is effective through a transparent place in the cube by tomagraphic means or a multiple array planar detector.

As discussed in the introduction the resolution power of a chromatographic technique is better defined by the number of components which can be resolved from its neighbors with a resolution unity and the time requested. Conventional column chromatography has a peak capacity which in current practice cannot exceed 150–200 and in exceptional cases 500. This last performance would require the equivalent of a million theoretical plates, well beyond reach even using the best capillary columns we may dream of. The spot capacity of TLC is in practice limited to about 30. To achieve better capacity would require the use of very long plates with prohibitively long development times and large tanks. In over-pressure TLC the spot capacity becomes comparable to that achieved in column chromatography (CC); only the available pressure drop (limited by the maximum allowable over-pressure) and the length are really limiting the capacity, much as in CC. With the 30 cm long plates used by Tyihak et al a spot capacity of about 80 is a practical maximum (particule size: 5 micrometers, h=2 pressure: 36 atm).

On the other hand $(TLC)^2$ offers a spot capacity of about 300 without any major difficulty: a $10 \times 10$ cm plate made with 15 micrometer particles will do and the total development time is around 30 min. with most solvent combinations. It becomes extremely difficult to reach a capacity of 500, however, again because of the problems associated with the quadratic law of solvent front migration. One should force the solvent through the chromatographic bed and not trust capillary forces to do it.

When the two-dimension chromatographic bed is operated according to our invention, the peak capacity is again markedly increased. Scanning a range of $k'$ extending from 0 to 10, one can, in principle, achieve a peak capacity of 750 with a $10 \times 10$ cm column packed with 10 micrometer particles, with a packing quality comparable to that of good CC columns. As it is easier to pack a homogeneous thin-layer than a homogeneous cylinder a better peak capacity, up to about 900 could be achieved. This column has to be operated at a relatively large reduced velocity ($\nu$ about 10) so the lateral spreading of the spots is reduced markedly in a trading with increased axial broadening. With a typical compound with a diffusion coefficient of $5 \times 10^{-6}$ cm$^2$/s and a solvent of viscosity 1 cP, the actual solvent velocity is 0.05 cm/s, the inlet pressure 5 atm and the breakthrough time 200 s. Total analysis time ($t_0$ in the first direction and 11 $t_0$ in the second one to scan $k'$ from 0 to 10) is 40 min. The bursting force on the column wall is 500 kg.

Much better performances can be achieved using a very well-paced (A=0.70) column, $15 \times 15$ cm made with 3 micrometer particles. This provides a capacity of 4600 peaks, with a total analysis time of 18 min. with an inlet pressure of 280 atm, so the over-pressure bursting force in the equipment is at least 63 tons.

Accordingly the practical limit in peak capacity of $(CC)^2$ is a few thousands, about 10 times larger than either CC or $(TLC)^2$.

Those skilled in the art will understand that many different retention mechanisms may be utilized, chosen for their respective appropriateness to the unknown being analyzed. Furthermore, many different detectors may be employed, such optical detectors for detecting changes in the index of refraction, polarization rotation and the like. If the materials being analyzed are radioactive or are made radioactive, radiation detectors may be employed. Fluorescence detectors and detectors of any approproate physical phenomena, such as hot wire or flame detectors, may be utilized.

The invention also contemplates that one or more of the separation steps may be carried out with a gas rather than a liquid. Thus the first step could be carried out by gas chromatography until the first constituent reached the edge of the packed linear column and the second orthogonal step carried out by eluting a gas through the two-dimensional plate-like column. Liquid and gas chromatography could be used alternatively, either one first. Fluid is used herein to mean liquid or gas.

Each dimensional separation except the last can be carried out using conventional thin-layer chromatography without over-pressure—the last dimensional separation utilizing over-pressured fluid (gas or liquid) chromatography with a real-time multiple linear array detector (in the case of two-dimensional chromatography) or a real-time multiple planar array or tomagraphic detector (in the case of three-dimensional chromatography).

Similarly, each dimensional separation except the last can be carried out using electrophoresis or any other chromatographic separation process.

OBJECTS OF THE INVENTION

It is therefore an object of the invention to provide multi-dimensional chromatographic systems and apparatus.

Another object of the invention is to provide such systems and apparatus utilizing real-time detection of constituents eluting over a period of time.

A further object of the invention is to provide such systems and apparatus utilizing successively different retention mechanisms.

Still another object of the invention is to provide such systems and apparatus providing output data which may be conveniently analyzed by means of digital computers.

Yet still another object of the invention is to provide such systems and apparatus providing for three-dimensional chromatography.

A further object of the invention is to provide such systems and apparatus utilizing gas or liquid chromatography or electrophoresis or combinations thereof.

Another object of the invention is to provide such systems and apparatus which decrease the time required for analysis.

Still another object of the invention is to provide such systems and apparatus which may utilize conventional thin-layer chromatography for separation in any dimension but the last.

Yet another object of the invention is to provide such systems and apparatus which utilize over-pressured thin-layer chromatography or gas chromatography for the last dimensional separation.

A further object of the invention is to provide such systems and apparatus providing for more accurate detection of constituents of an unknown.

A still further object of the invention is to provide such systems and apparatus for providing more accurate measure of the quantities of various constituents of an unknown.

Other objects of the invention such as speeding up and automating the process of multi-dimensional chromatography will in part be obvious and will in part appear hereinafter.

The invention accordingly comprises the several steps and the relation of one or more of such steps with respect to each of the others and the apparatus and systems embodying the features of construction and arrangements of parts which are adapted to effect such steps, all as exemplified in the following detailed disclosure. The scope of the invention is indicated in the claims.

BRIEF DESCRIPTION OF THE DRAWINGS

For a fuller understanding of the nature and objects of the invention reference should be had to the following detailed description taken in connection with the accompanying drawing in which.

The same reference characters refer to the same elements throughout the several views of the drawing.

BEST MODES FOR CARRYING OUT THE INVENTION

Figure 1:
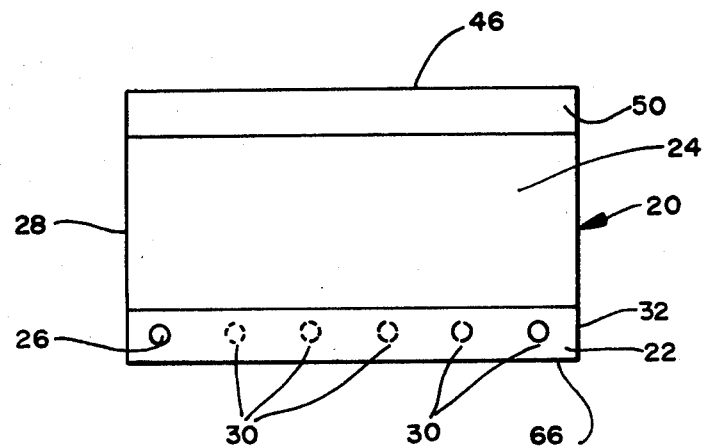
FIG. 1 is a top plan view of a two-dimensional thin-layer chromatographic plate utilized in the invention.

Now referring to FIG. 1, a conventional two-dimensional bi-phase chromatographic plate 20 used in the invention may comprise a glass plate of which a first band or strip 22 of plain silica gel is affixed, the remaining portion of the plate 24 is also covered with silica gel; however, this has been treated to react to the OH groups bonded to the silica with octadecyl ($C_{18}$) alkyl groups. Thus, the strip 22 has a normal silica surface which is highly polar, and it interacts with components of the unknown by means of their polar groups. The surface 24 is alkyl-bonded silica which is poorly wetted by water, non-polar, and interacts essentially with the alkyl or carbon skeleton of the molecule.

The unknown 26 is placed at one end of the strip 22 and the edge 28 may be wetted by an appropriate non-polar or moderately polar solvent, like heptane or chloroform. The constituents of the unknown 26 will thus differentially move along the strip 22 and be separated into the constituents indicated by the dotted spots 30. When a dotted spot has reached edge 32 of plate 20 the development is stopped and the plate dried.

Figure 2:
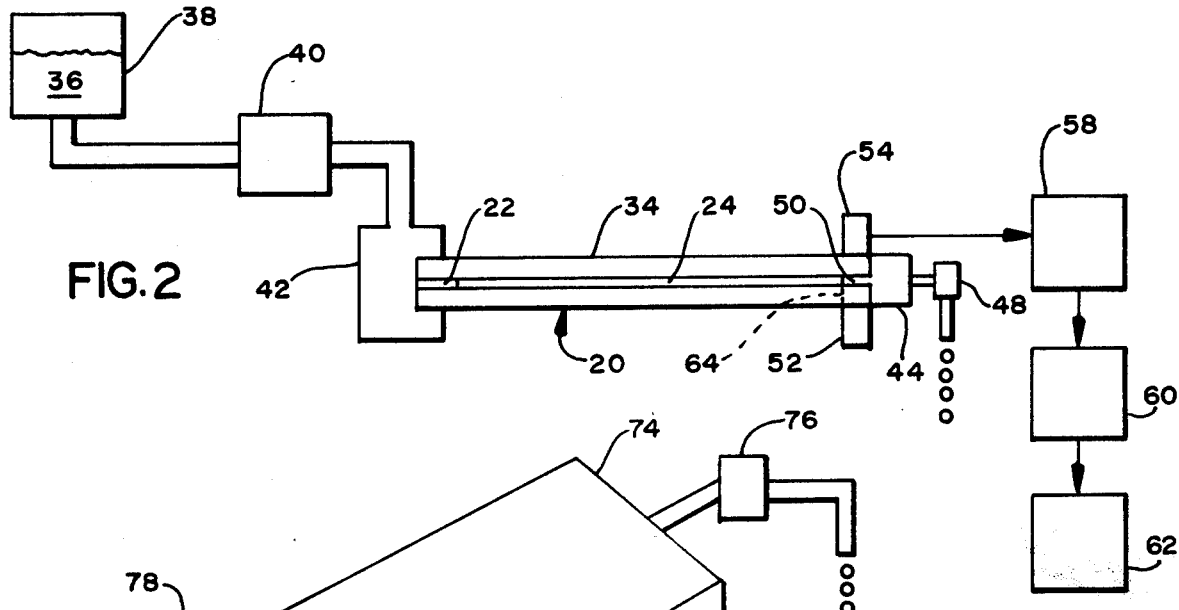
FIG. 2 is a diagrammatic view of over-pressured elution apparatus and real-time detection means utilized in the system and apparatus of the invention.

Now referring to FIG. 2, the plate 20 is then inserted into apparatus for over-pressured development. A cover plate 34 is provided in contact with the silica gel 24 and 22.

An appropriate solvent 36 for the retention mechanism of the alkyl bonded silica gel 24, such as water, methanol, acetonitrile, or mixtures thereof, is supplied from reservoir 38 to a pump 40 and from the pump 40 to a plenum chamber 42 which forces the solvent 36 through the strip 22 and the thin plate-like column of silica gel 24. The pressure in the plenum may be several (up to at least 15) atmospheres. A second plenum 44 at the edge 46 of plate 20 may be connected to a vacuum pump 48 to aid in the elution of the solvent 36 through the planar column of FIG. 2. The solvents mentioned will move at an average rate of about one millimeter per second under these conditions.

Now referring to FIG. 1, a strip 50 at edge 46 of plate 20 is preferably not covered with silica gel 24 and the plate is preferably of glass or quartz. This allows detection of the eluting components in FIG. 2 by passing light through the glass or quartz cover plate 34 and through the transparent strip 50 of plate 20.

Light source 52 illuminates the eluting solvent 36 and components of the unknown and this is detected by detector 54 which may be a linear multi-photo diode array.

Since these arrays come in lengths of about 2½ centimeters, and the conventional plates 20 are approximately 10 centimeters on an edge, an optical system (not shown) may be utilized to focus the image of the strip 50 onto the detector 54. The detector, which may have several thousand diodes, is connected to an analog-to-digital converter and commutator 58 which converts the outputs of each of the diodes to digital form and supplies them at frequent intervals, for example, ten times per second, to a multi-channel tape recorder 60. The rate at which the output of the diode array 54 is recorded by the tape recorder 60 depends of course upon the speed of elution of the solvent 36 and the components of the unknown. Under the conditions stated above each constituent peak is a spot 0.5 to 3 millimeters in diameter. It is preferred that this be fast enough so that a large enough number of readings of the rise and fall of the peak of each component being eluted is recorded so that an integration may be performed of the total size of the peak, thus giving an accurate indication of the quantity of the component. The literally millions of individual measurements recorded on the magnetic tape 60 are then supplied to a large digital computer 62 which converts data either to a pseudo-three-dimensional plot which simulates the components as mountain peaks on a two-dimensional plate, or a listing of components derived from previous test measurements with the quantity of each found, or to a two-dimensional chromatogram similar to a developed bi-phase plate.

Each side of the plate 20 of FIG. 1 may be 5 to 20 centimeters long and the silica gel, layers 22 and 24 thereon, may be 1/10th to one millimeter thick. The plate 20 is thus conventional except for the transparent strip 50 along the top edge 46 thereof. When no such strip is provided the apparatus of FIG. 2 may be provided with its own window as indicated at the dotted line 64.

The first development of the components 30 along the strip 22 may be performed as described by conventional thin-layer chromatography, or the apparatus illustrated in FIG. 2 may be used, in which case an appropriate solvent 36 is forced into the edge 28 perpendicular to the strip 22 and the development continues until the first component is detected by the detector 54. The development is then stopped. The plate dried. Then the plate is again placed into the apparatus of FIG. 2 with the lower edge 66 in the plenum 22.

It will be understood that the edges of the plate 20 and the cover plate 34, not within the plenum 42 or plenum 44, are sealed to prevent leaks.

The apparatus of FIG. 2 may be thought of as many intercommunicating parallel chromatographic columns and in fact, the solvent 36 need not be a liquid, but could be a gas and the apparatus of FIG. 2 could operate by gas chromatography.

The light source 52 may be ultraviolet at 254 nanometers, in which case plate 34 and window 50 are quartz. Alternatively, there may be a plurality of light sources which are successively illuminated, such as 254, 280 and 350 nanometers, these wave lengths being chosen to be specifically absorbed by the unknown constituents being sought. The measurements at the three different wave lengths can then be utilized to make three superimposed plots on a TV screen, each in a different primary color. In this way constituents of an unknown mixture may be recognized by their colors in the three color presentation of the chromatogram.

Those skilled in the art will understand that the retention media 22 and 24 need not be conventional thinlayer chromatographic retention media in the apparatus of FIG. 2, but may be any kind of stationary phase used in liquid chromatography, as for example gels used for gel or size exclusion chromatography. Also, other means such as the application of electrical fields as used in electrophoresis, to induce separation of components of a mixture, may also be employed. Furthermore, if gas chromatography is utilized, any of the well known packing materials utilized in packed gas chromatographic columns may be employed.

Many different forms of detection may be utilized in the apparatus of FIG. 2 other than the straight densometry mentioned above. Conventional means may be employed for detecting the index of refraction of the eluting mixture. If the components fluoresce, fluorescence detection may be employed. The components may be radioactive or may be tagged with radioactive molecules, such as in various radioassay techniques, and the detector 54 may be a radioactivity detector. The components may be ions and the detector 54 may be an electro-chemical detector.

If the moving phase medium 36 is a gas, various detectors used in gas chromatography may be used, such as flame detectors or hot wire detectors.

Those skilled in the art will see that we have provided a method of greatly increasing the number of constituents which may be separated from an unknown mixture in less time and with a real-time output capable of being analyzed by data processing techniques.

Depending on the size of plate and size of particles used to pack the column as well as packing qualities, the number of components that may be separated from a mixture according to the apparatus of FIG. 2 may be as high as five hundred to more than one thousand in a single two-phased chromatographic analysis.

Figure 3:
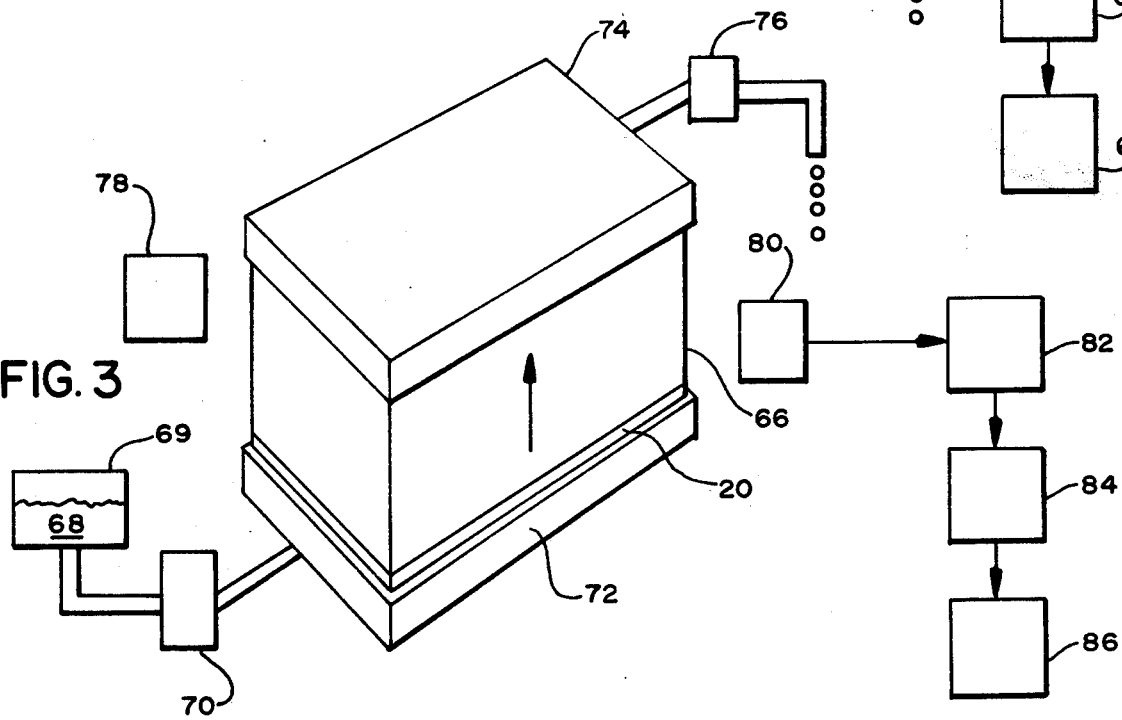
FIG. 3 is a diagrammatic view of a system and apparatus for automatic three-dimensional chromatography according to the invention.

The system and apparatus of our invention may be generalized to three dimensions as illustrated in FIG. 3. There the chromatographic plate 20 is not made of glass but of a completely porous substance. After being developed in the second dimension (that orthogonal to the strip 22) until the first component reaches the detector 54 development is stopped and the plate 20 is dried.

It is then placed against a cube 66 of a stationary phase of a third retention mechanism and then appropriate moving phase 68 for that retention mechanism is pumped from reservoir 69 by pump 70 through plenum chamber 72 into one face of the cube 66 and thence through the cube 66 in the direction of the arrow to the opposite face of the cube 66 and into an evacuation plenum 74 and vacuum pump 76. Of course the other faces of the cube are sealed by means not shown. Detection of the exiting components in a plane perpendicular to the arrow may be accomplished by a tomagraphic detector comprising a light source 78 rotating in the plane with detector 80. Information is fed to an analog-to-digital converter commutator 82 and then to magnetic tape recorder 84 and thence may be analyzed by a digital computer 86 in the same manner utilizing the same tomagraphic equations presently used in medical tomagraphy. Alternatively, a planar array detector may be incorporated into the plenum 74.

Utilizing the apparatus illustrated in FIG. 3, as many as ten thousand components may be separated from a single unknown by a single three-dimensional chromatographic analysis.

Figure 4:
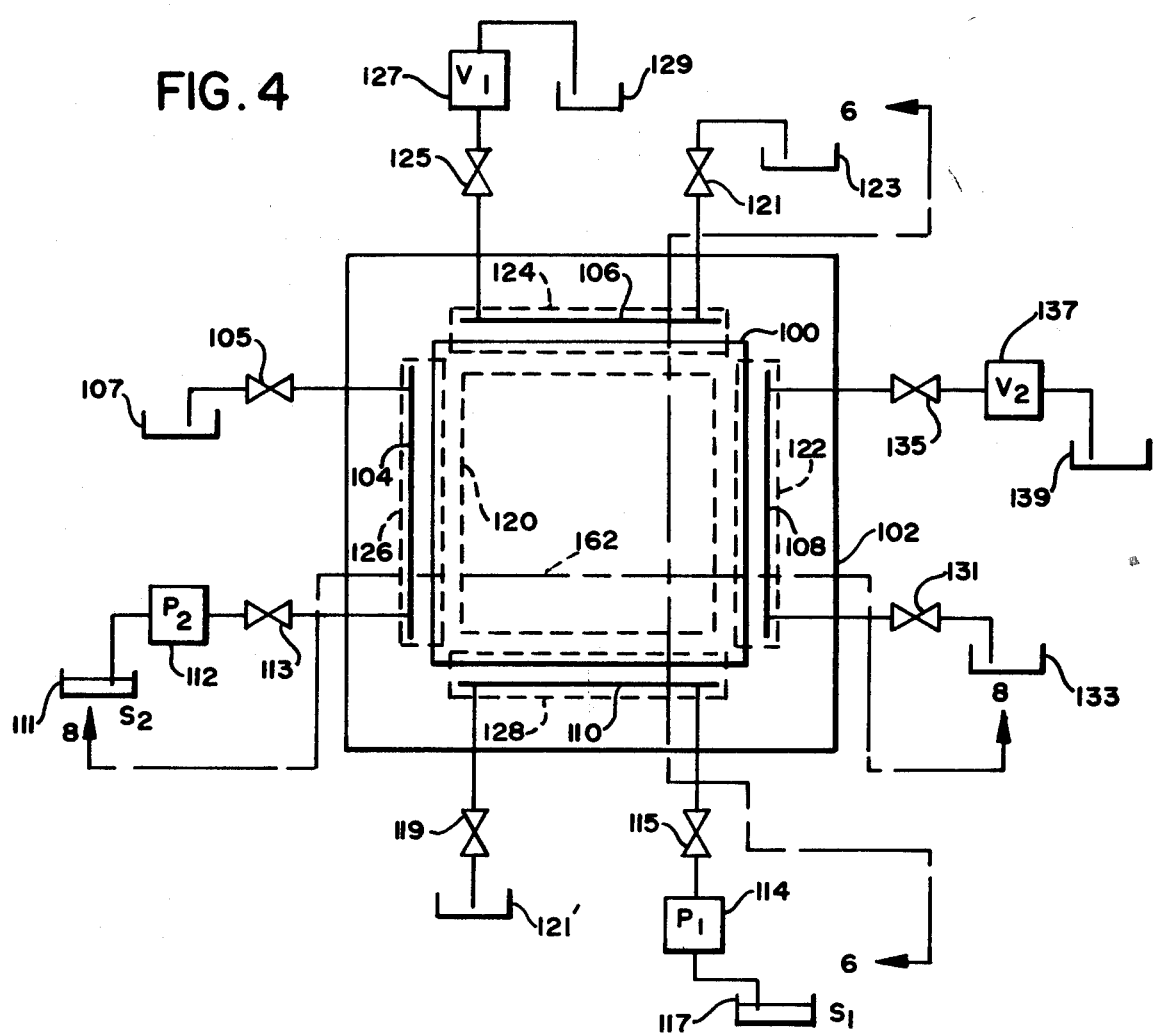
FIG. 4 is a plan view of apparatus for performing two-dimensional column chromatography, two-dimensional thin column chromatography and multi-sample thin column chromatography according to the invention.
Figure 5:
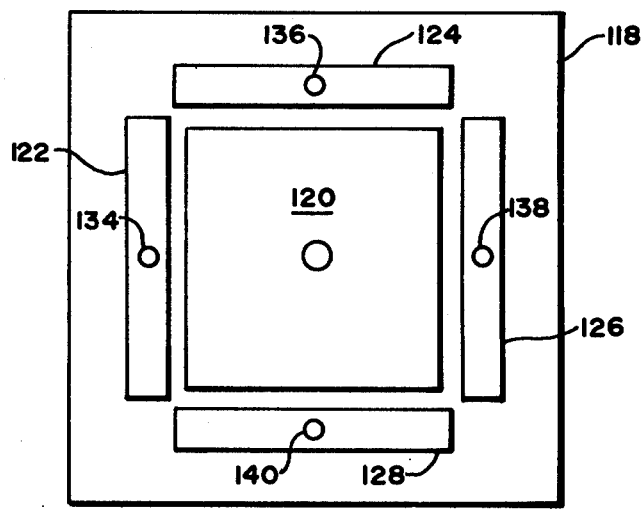
FIG. 5 is a bottom view of a portion of the apparatus of FIG. 4.
Figure 6:
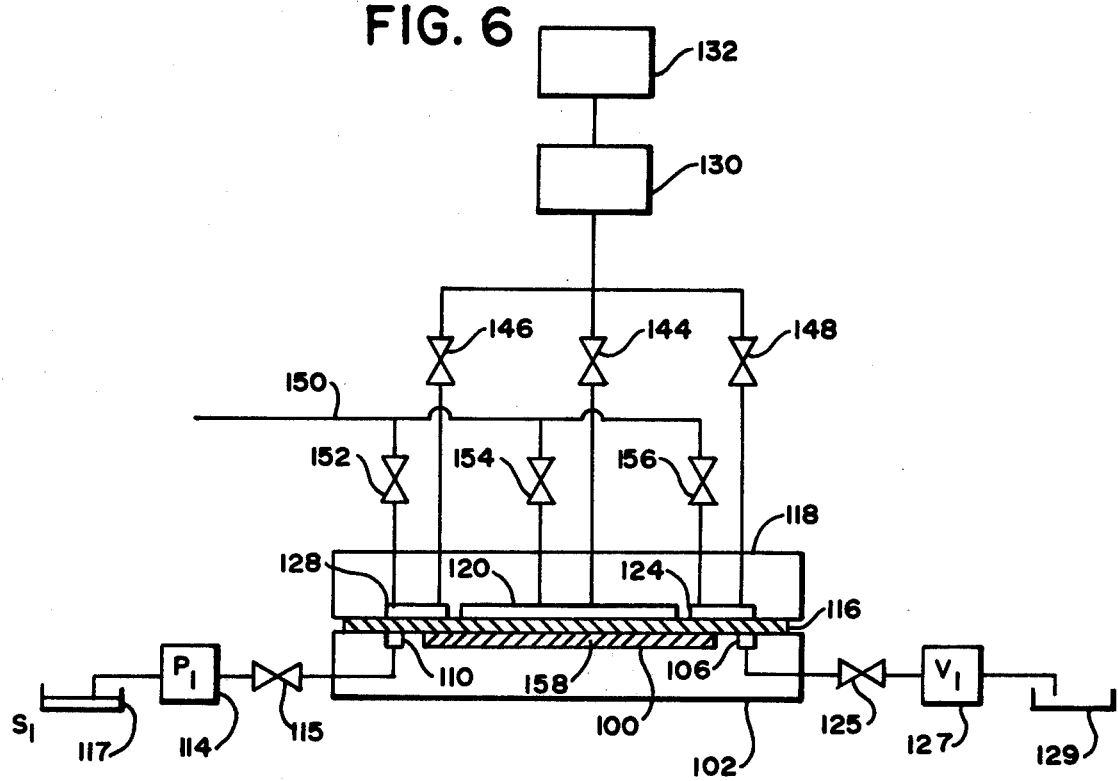
FIG. 6 is a cross sectional diagrammatic view taken along the line 6—6 of FIG. 4.

More particularly and referring to FIGS. 4, 5, and 6, preferred apparatus for over-pressure two-dimensional thin column chromatography (TCC)$^2$, two-dimensional over-pressure continuous column chromatography (CC)$^2$ and over-pressure multi-sample thin column chromatography (MTCC) comprises a steel cuvette 102. This may be 15 cm square and 5 cm thick. A 10 cm square, 1 mm deep, cavity 100 is machined in the block 102. It is filled with a slurry of the particles chosen for the chromatographic bed, suspended in an appropriate solvent. A slight excess of the slurry is used and when it is settled sufficiently, but before the solvent has evaporated, the excess is scraped off by passing a microtome blade over the block 102. The bed is dried in an oven and placed in a hood.

The block 102 also has machined in it four 1 mm wide, 1 mm deep, 10 cm long, grooves 104, 106, 108, and 110, each located 3 mm from and parallel to one of the edges of the cavity 100. Groove 104 is connected to a solvent supply comprising a reservoir 111, pump 112, and valve 113. Groove 110 is connected to a solvent supply comprising pump 114, valve 115, and solvent reservoir 117. Groove 104 is connected at its opposite ends through valve 105 to a collection reservoir 107. Thus groove 104 may be purged by opening valves 105 and 113 and turning on pump 112. Groove 110 may be similarly purged by using valve 119 and collection reservoir 121. Thus grooves 104 and 110 are the supply grooves for the apparatus.

Grooves 106 and 108 are the collection grooves. Groove 106 is connected through valve 121 to collection reservoir 123 and through valve 125 through suction pump 127 to collection reservoir 129. Similarly collection groove 108 is connected through valve 131 to collection reservoir 133 and through valve 135 via suction pump 137 to collection reservoir 139. Thus collection grooves 106 and 108 may be drained, subject only to the pressure of the eluting fluid through valves 121 and 131 respectively, or negative pressure may be applied to grooves 106 and 108 by means of the suction pumps 127 and 137 respectively.

Pumps 112 and 114 are conventional Waters 6000A HPLC pumps, manufactured by Waters Associates, Milford, Mass.

Referring now to FIG. 6, a thin sheet 116 of mylar or other flexible material resistant to the solvent used, is placed over the steel block 102 and a 15×15×5 cm block 118 of plexiglass is tightly pressed against block 102 using seven bolts (not shown).

Referring to FIG. 5, the face of the plexiglass block 118 pressed against the mylar sheet 116 is machined. Central cavity 120 is 9.8×9.8 cm. Grooves 122, 124, 126, and 128 are 5 mm wide, each parallel to a side of the central cavity 120 and spaced about 1 mm from it. Cavity 120 and grooves 122, 124, 126, and 128 are about 2 mm deep and are connected via channels 134, 136, 138, 140, and 142 to a source of water under pressure 130 (FIG. 6) fed by water pump 132. The water under pressure is fed via five valves, (only three, 144, 146, and 148 are shown) to the five cavities in the plexiglass block 118. The five cavities are also connected to vacuum line 150 via five valves, (only three valves 152, 154 and 156 are shown).

Referring particularly to FIG. 6, in performing the first separation, valve 144 would be open to supply water under pressure to cavity 120, firmly pressing the mylar sheet against the separation medium 158. Valve 154 would be closed. Valves 146 and 148 would be closed, and valves 152 and 156 opened, applying vacuum to grooves 124 and 128.

Figure 7:
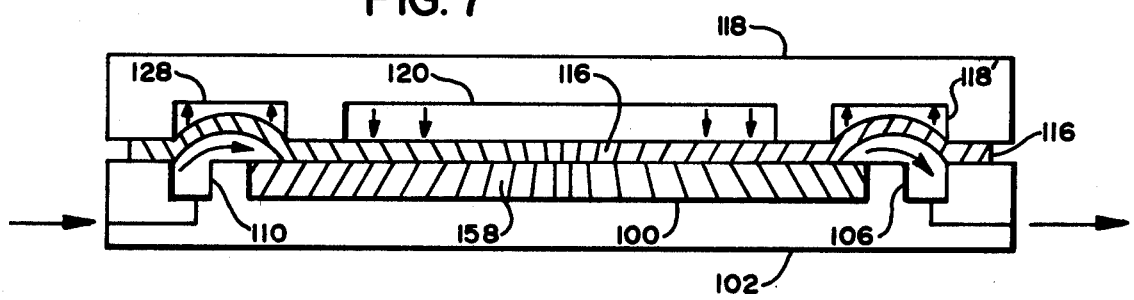
FIG. 7 is a cross sectional view taken along the line 6—6 of FIG. 4.

Now referring to FIG. 7, this causes the mylar above grooves 110 and 106 to lift up, providing a connecting path between the grooves 110 and 106, and the medium 158.

The corresponding valves to grooves 104 and 108 would be in their opposite state such that water under pressure would be applied to those grooves closing off any path between the medium 158 and those grooves.

Figure 8:
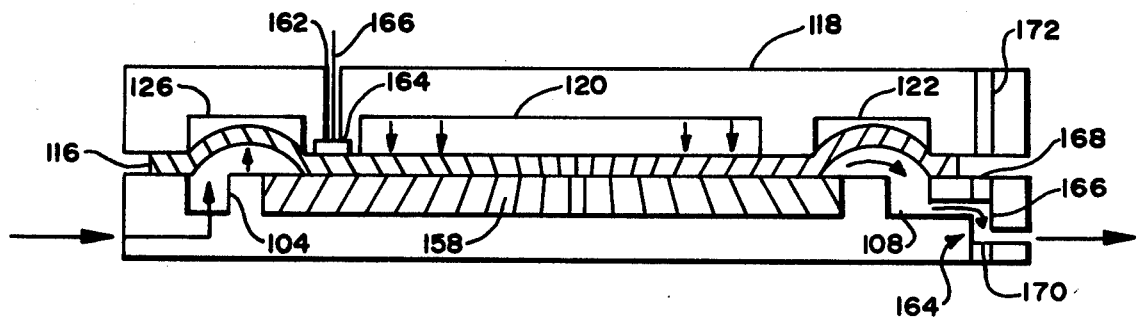
FIG. 8 is a cross sectional view taken along the line 8—8 of FIG. 4.
Figure 9:
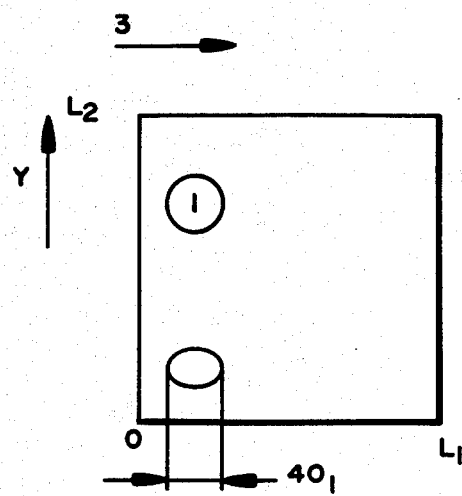
FIGS. 9 through 14 are planar diagrammatic views of a two-dimensional chromatographic plate illustrating spot migration and growth.
Figure 10:
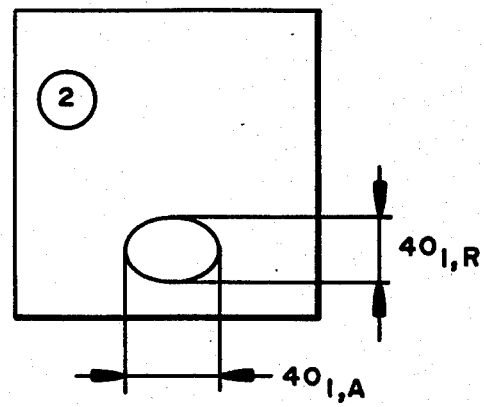
Figure 11:
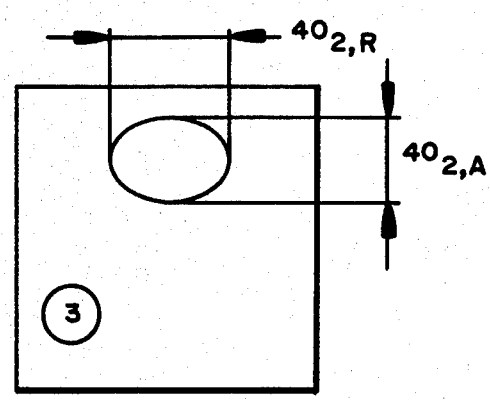
Figure 12:
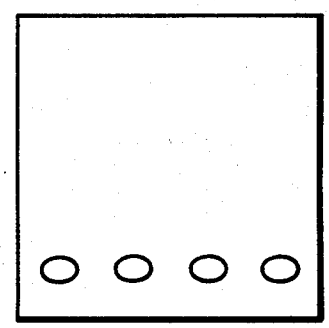
Figure 13:
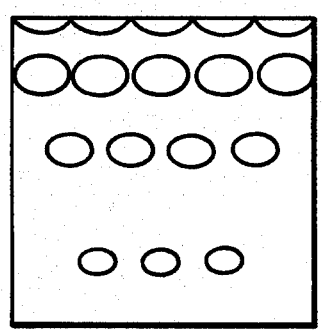
Figure 14:
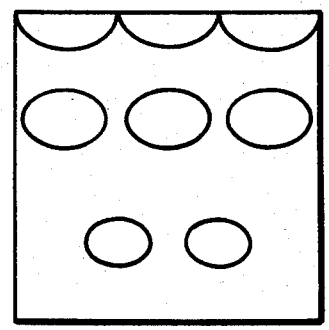

Now referring to FIG. 8, a sampling port 162 is provided in the plexiglass block 118. It is terminated with a septum 164 such that a hypodermic needle 166 may be inserted therethrough to inject a sample into the medium 158 after the solvent is flowing through it. The solvent flow is continued until the first constituent of interest reaches the opposite edge of cavity 120. The solvent flow is then terminated.

For the second separation, water is applied under pressure to grooves 124 and 128 and vacuum is applied to grooves 122 and 126. Solvent is then pumped through the medium 158 from groove 104 to groove 108.

As shown in FIG. 8, groove 108 is provided with a tortuous sheet-like exit path generally indicated at 164 such that the solvent continues to flow in a laminar fashion and in a downward path at 166. Quartz windows 168 and 170 are provided at the opposite ends of path 166. Similarly a slot 172 is provided above quartz window 168 so that light may pass through slot 172, quartz windows 168 and 170, and flow path 166 for detection of the eluting constituents.

This system is very simple, leak proof up to 8 to 10 atmospheres, reliable and provides excellent results. The bed efficiency is excellent, with reduced efficiency as low as 2. Even with a column thickness of 1 mm there appears to be no significant radial gradient of flow velocity except at pressures very close to the over-pressure provided by the water. The flow profile is nearly constant across the column except within a few millimeters from the edges. We prefer to locate the port 166 about 1 cm from the edges of cavity 120 to avoid perturbations in the flow velocity along the column edge. Once injected the sample spot should have a diameter smaller than 1.2 mm to minimize its contribution to the final spot size.

An ultraviolet monochromatic light beam at 254 nanometers is provided by a powerful mercury lamp, a large parabolic mirror and a 9 cm×0.5 mm slit (not shown). This parallel beam is focused through slot 172, quartz windows 168 and 170, the flowing stream 166, onto a 1 inch long 1024 Pixel array detector (not shown) supplied by Redicon of Sunnyvale, Calif. This is the equivalent of 1024 conventional ultraviolet detectors used in chromatography with a 1 mm optical path length. The lens has a 1 meter focal length and the system provides a definition of 1 pixel oer most of the slit, 2 pixels at the very edge; that is, 0.09 and 0.17 mm respectively. At the beginning of elution, the standard deviation of the spots at the column exit is usually around 1.5 mm. Thus, 10 data points are provided per each standard deviation at the beginning of elution. As the elution progresses, the spots get wider and the density of data points increases.

The diode array is scanned 10 times per second at a flow velocity of 0.05 cm per second, this provides 30 data points per standard deviation at $k'=0$ and many more at $k'=10$. The measurements can be added in groups of three at first and then more to improve the signal to noise ratio. A Hewlett Packard model 21MX supplied by Hewlett Packard, Palo Alto, Calif., corrects the signals of each individual pixel for base current response. The data may then be recorded on magnetic tape or immediately processed by computer to provide a real-time visual display.

Alternatively, the eluting output of the second development can be scanned through slot 172 (FIG. 8) by means of a scanning ultraviolet beam and a single detector or a scanning Vidicon may be used in place of the diode array.

The processing of the output of the diode array, the flying spot scanner or the Vidicon is done in the same way that electrophoretic chromatograms are scanned in the prior art to provide enhanced visual displays.

The apparatus illustrated in FIGS. 4-8 may also be used as a multi-column chromatograph for many samples. Referring to FIG. 4, in this case solvent flow is provided from groove 104 to groove 108 and many individual samples are injected through many sampling ports similar to sampling port 162, arrayed in a line parallel to groove 104 and spaced about 1 cm from the edge of cavity 120 adjacent to groove 104.

The apparatus may also be used to over-pressure develop two-dimensional chromatograms which are read in a conventional fashion by stopping the second development when the first spot of interest reaches the edge of cavity 100 adjacent output groove 108. The advantages over the prior art are achieved by injecting the unknown after solvent flow is established in the first development and by over-pressure development in both directions.

SIGNAL ACQUISITION AND PROCESSING

After elution through the column, the liquid phase passes through slit 166 (FIG. 6) which may be 1/10th mm thick, 10 cm long and 5 mm deep. This is the detector cell in which the effluent flows steadily. The dimensions of the slit and the geometry of the exit line are designed to minimize turbulence in the liquid so as to obtain a "curtain flow" such that the spot broadening by remixing of the liquid is negligible.

A monochromatic ultraviolet light source at, for example, 254 nanometers illuminates the cell 166 and the transmitted light falls on a monolithic self-scanning charge coupled device photo diode array. This off-the-shelf item consists of a row of silicon photo diode each with an associated storage capacitor on which to integrate photo current and a multiplex switch for periodic readout by an interated shift register scanning circuit.

The array we use (available from Reticon of Sunnyvale, Calif.) has 1,024 elements (pixels), each cell consists of a photo diode and a dummy diode, both with an associated storage capacitor. These diodes are connected through multiplex switches to video and dummy recharge lines common to all cells.

The scanning circuit is driven by a single phase clock with a start pulse to initiate the scan. The clock frequency defines the cell-to-cell rate. The time interval between two scans is defined by the time elapsed between two start pulses. The charges stored on each photo diode is gradually removed by photo current during the line time. The photo current is the product of the line sensitivity and the irradiance. The total charge removed from each cell is the product of the photo current and the line time. This charge is sent through the video line when the diode is sampled and reset once each scan.

Figure 21:
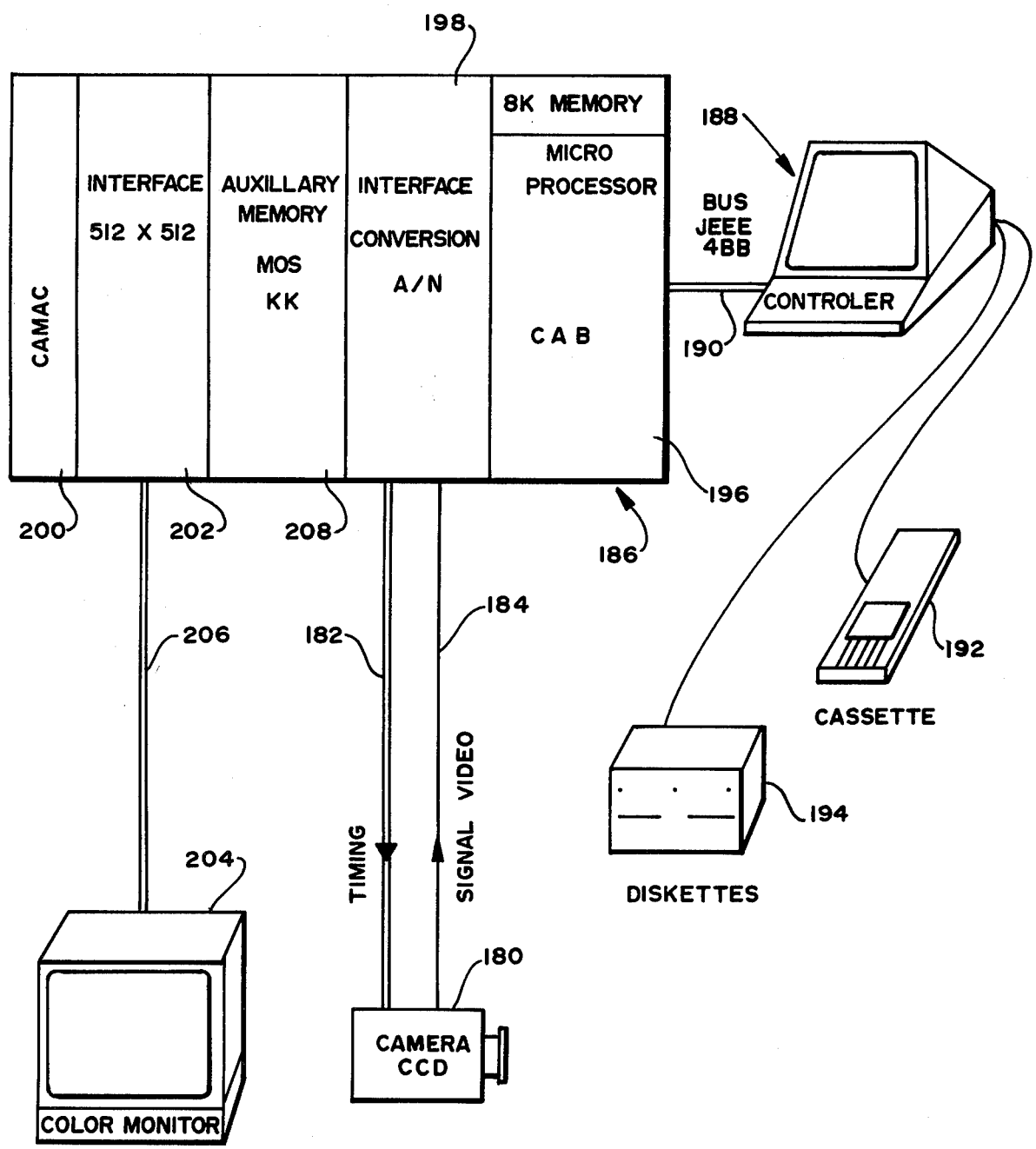
FIG. 21 is a schematic block diagram of a data acquisition and processing system according to our invention.

Now referring to FIG. 21, the charge couple diode array is shown at 180; the clock lines at 182 and the video signal line at 184. They are connected to a computer processing unit generally indicated at 186. A video console generally indicated at 188 is connected to the processor 186 via an IEEE488 line 190. Mass storage devices such as a cassette recorder 192 or a diskette unit 194 may be connected to the video terminal 188.

As the liquid flows through the slit, its local composition in the detector cell 166 (FIG. 8) varies as time elapses. It is necessary to correctly represent the elution of the spots to get the same temporal resolution as they pass by as spatial resolution if the elution were stopped and they were read conventionally. The 1024 pixels are arranged in the optical system such that they look at 50 micrometers along the length of the cell 166 which provides 20 sampling data points per millimeter.

When the flow of the liquid through the slit is optimized to provide maximum separation of the different constituents as discussed below in the section THEORY, it is necessary to perform one scan every 1/10th of a second. A complete separation can take about 15 minutes, approximately 1,000 seconds. This will thus require about 1,000 scans at 10 Hertz. The quantity of data to be stored is thus about 10 million values.

Because of the above constraints, the interfacing and data acquisition system must be very fast as it must convert and read one scan and then process and store or visualize it in less than 100 milliseconds. The system discussed below is able to meet these requirements and even would provide for faster data acquisition, for background correction, diode callibration, signal filtering, and all functions commonly used in any data acquisition unit.

The video signal has to be amplified, filtered and processed and the information must be stored.

Again referring to FIG. 21, the system we provide has a microprocessor 196 which manages all of the functions required for a given application. The microprocessor 196 can be activated by the terminal 188 via the IEEE488 bus 190. The terminal 188 performs the function of cross-assembling the microprocessor programs, loading the programs into the system microprocessor 196 for a given sequence and entering data for the program to be run, (e.g. start, sampling rate, sensitivity, gain, etc.). Such a system exists in the prior art using a CMB3032 or a Tektronics 404A or a Hewlett Packard 21MX computer.

The signal from the diode array 180 travels through the video line 184, interface and A to D conversion unit 198, differentially amplifies the video pulses to a usable voltage level. After the multiplex switch in the CCD180 is closed to sample the next diode, the voltage change on the video line 184 is sensed through a buffer amplifier in the interface and A to D conversion unit 198, sampled and held. The result is a boxcar shaped video signal which presents a differential current amplified signal which has the advantage of being an integrated signal and thus more easy to read and less noise sensitive.

The signal is then digitized through an analog-to-digital converter, for example, a TRW PDC 1007J. The conversion time of this unit for one word is 200 nanoseconds. The total photo diode array signal or "spectrum" is thus converted on about 200 microseconds. Thus nearly all of the 100 milliseconds between two scans is available for real-time processing or data transfer of each spectrum.

All of the above is carried out in the interface and A to D conversion unit 198 through which signals from the microprocessor 196 and the diode array 180 are transmitted, synchronized, made compatible and transferred.

The signal is then supplied to a stand-alone CAMAC acquisition and data processing unit (LeCroy Research Systems, Spring Valley, N.Y.) which can be operated as an intelligent sub-system of a main data acquisition system performing monitoring, callibration, diagnostic, data sampling and display functions independent of the main system. The CAMAC samples the input signal every 50 nanoseconds, digitalizing and storing up to 1,024 successive samples which a resolution of 8 bits. The CAMAC may be operated from an external or internal clock. 4K words of instruction memory together with 4K words of data memory are available to the microprocessor.

The CAMAC is generally indicated at 202, its power supply at 200.

The CAMAC 202 comprises an interface for a color terminal with a 512×512 screen resolution. The data display 204 connected to the interface via cable 206 is preferably a CDCT 3151 BARCO monitor. The interface was developed in France (D.E.I.N. CEN. SACLAY). It includes a dynamic memory of 250K words of 4 bits in which the image to be visualized is constituted point by point. The contents of the memory is continuously read and transferred via video line 206 to the color monitor 204 together with the image and line synchronization signals.

By means of this system there can be displayed up to 50.5 images per second in the interlaced mode which thus displays the whole screen in about 12 seconds. The interface is totally programmable from the microprocessor of the CAMAC 202. The dimensions of the screen may be either 37×37 cm or 51×51 cm. The system also has the ability to provide hard copy. 16K of auxiliary memory 208 may also be utilized by the CAMAC 202.

After the signal has been processed several functions are available. The CAB CAMAC module can perform background subtraction, peak recognition, data compresion and the like. The data can then be stored either on magnetic tapes or discs depending on the terminal 188 used to activate the system and also the quantity of information to be stored.

This system has the advantages of speed of acquisition, capability of data processing, flexibility and ease of programming.

THEORY

The Figures

FIGS. 9–14—Symbols, definitions and calculation principles. 9—sample spot, assumed to be circular;- 10—spot of a compound after migration parallel to the first direction;11—spot of a compound after migration successively along the first and second directions:12—at the end of the first development the resolution of the spots must be larger than 1 since they broaden by diffusion in the z direction during the second development and we want them to be resolved with a resolution 1 at the end of the analysis;13—in $(CC)^2$ the compounds are eluted out of the column. Retained compounds have broader spots, hence the spot capacity in the z direction decreases with increasing retention time;14—spot capacity in the z direction continues to decrease.

Figure 15:
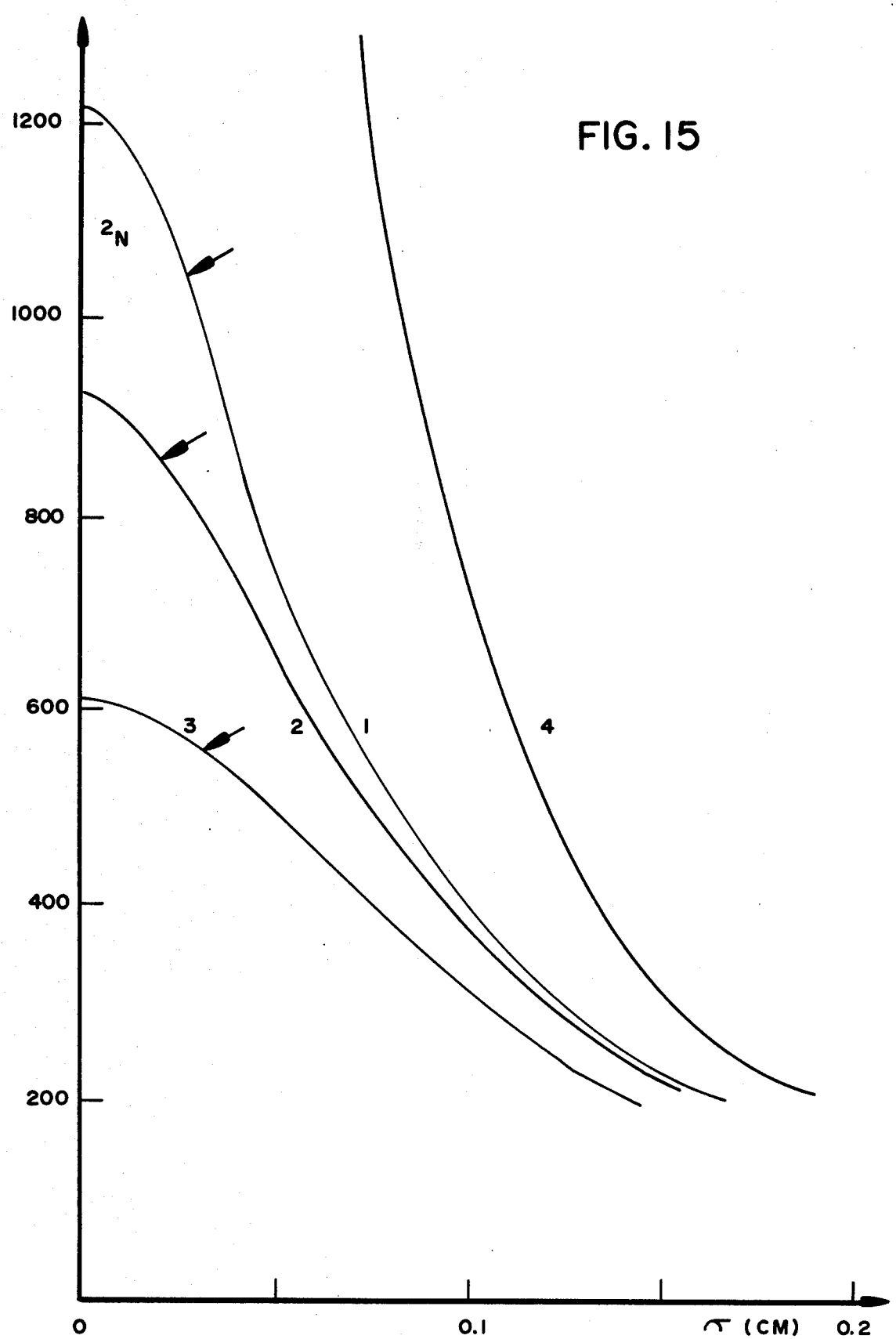
FIG. 15 is a plot of variation of the spot capacity in two-dimensional thin column chromatography against the standard deviation of the sample spot.

FIG. 15—Variation of the spot capacity in $(TCC)^2$ with the standard deviation of the sample spot. Column 10×10 cm. Other conditions in Table II. 1: $d_p=5$ μm, $v=8.9$; 2: $d_p=5$ μm, $v=2.6$; 3: $d_p=10$ μm, $v=8.9$. The arrows correspond to $\sigma_i^2/Ld_p=0.1$. 4: curve $n=L^2/16\sigma_i^2$ which is the upper limit to the spot capacity (see text).

Figure 16:
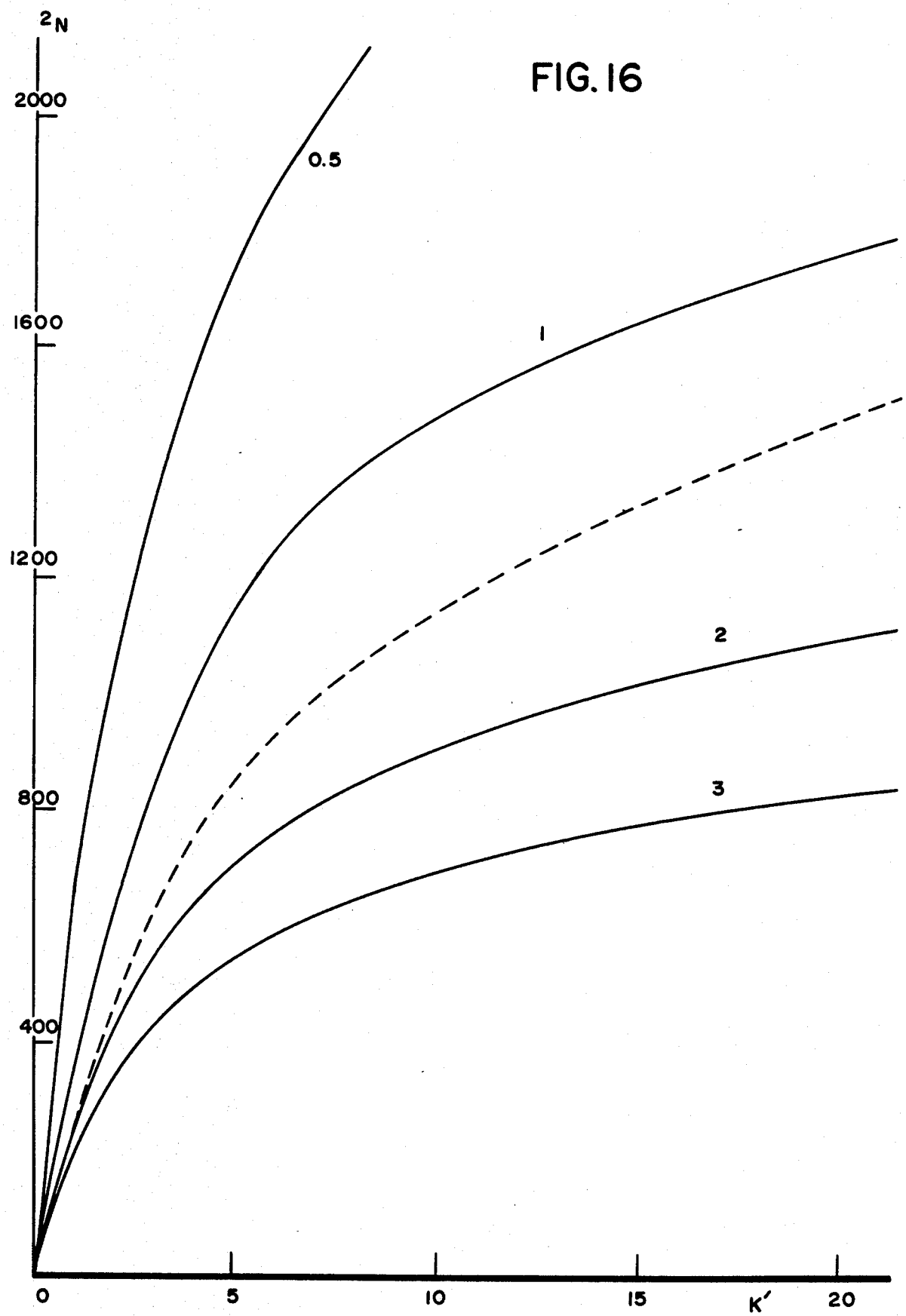
FIG. 16 is a plot of the peak capacity in two-dimensional column chromatography versus the value of k' at which the analysis is stopped.

FIG. 16—Plot of the peak capacity in $(CC)^2$ versus the value of k' at which the analysis is stopped. The value on the curve is the coefficient of packing homogeneity A in the plate height equation (Eq.15). The dotted line gives the peak capacity of a conventional column having $4\times10^6$ plates. Columns are 10×10 cm. $d_p=5$ μm. Reduced velocity, $v=7$.

Figure 17:
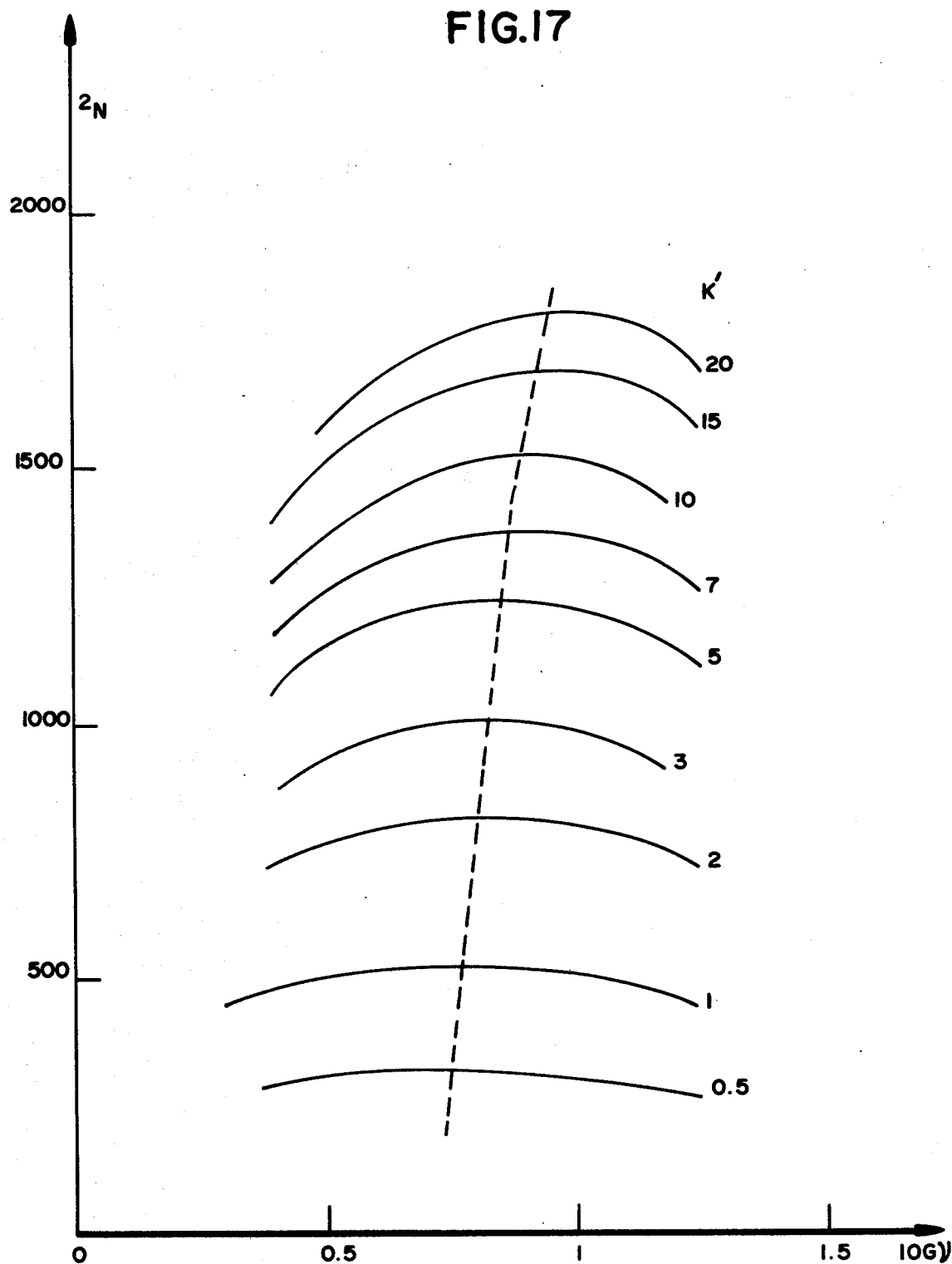
FIG. 17 is a plot of the peak capacity in two-dimensional column chromatography against the reduced velocity.

FIG. 17—Plot of the peak capacity in $(CC)^2$ vs the reduced velocity Column 10×10 cm. $d_p=5$ μm. The number on each curve is the value of k' at which the analysis is stopped. The dotted line indicates the maximum $\gamma=0.70$; $A=1.0$; $C=0.03$.

Figure 18:
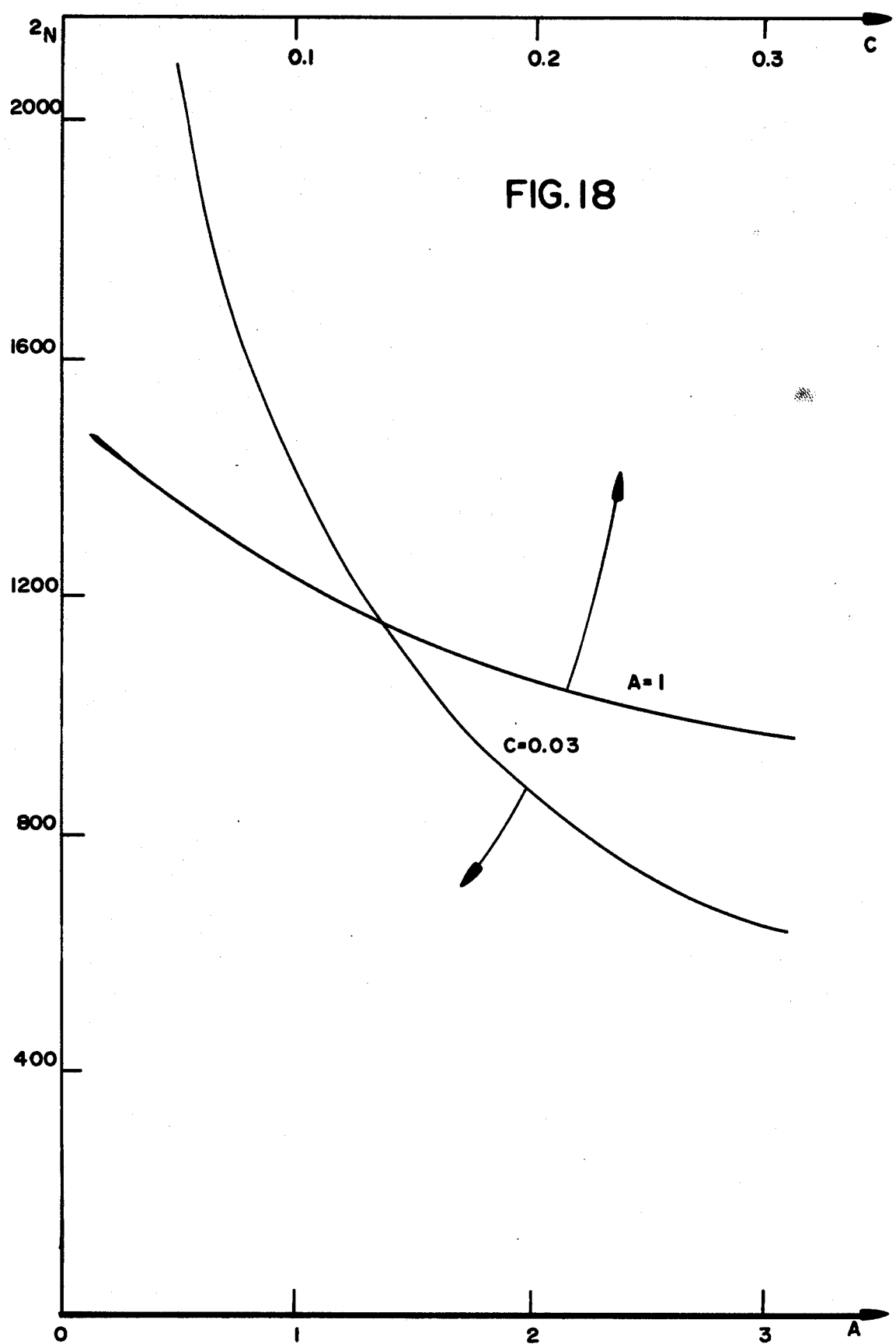
FIG. 18 is a plot of the peak capacity in two-dimensional column chromatography versus the value of the constants A and C.

FIG. 18—Plot of the peak capacity in $(CC)^2$ vs the value of the constants A (steeper curve, obtained with $C=0.03$) and C (obtained at $A=1$). In both cases $k'=7$; $v=7.0$; 10×10 cm column pakced with 5 μm particles.

Figure 19:
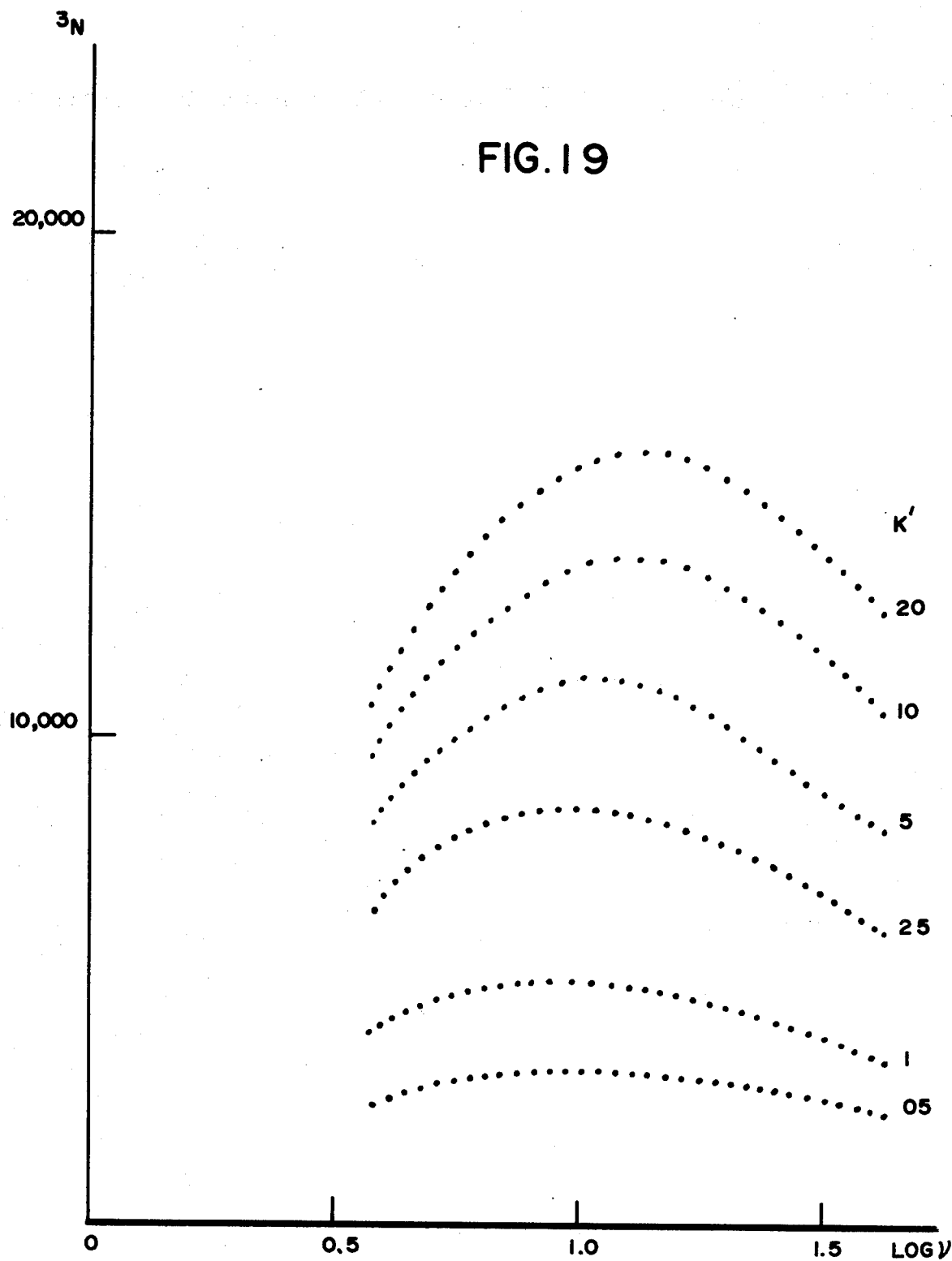
FIG. 19 is a plot of the peak capacity in three-dimensional column chromatography versus the reduced velocity.

FIG. 19—Plot of the peak capacity in $(CC)^3$ vs the reduced velocity. Column 10×10×10 cm. $d_p=10$ μm. The number on each curve is the value of k' at which the analysis is stopped. $\gamma=0.70$; $A=1.0$; $C=0.03$.

Figure 20:
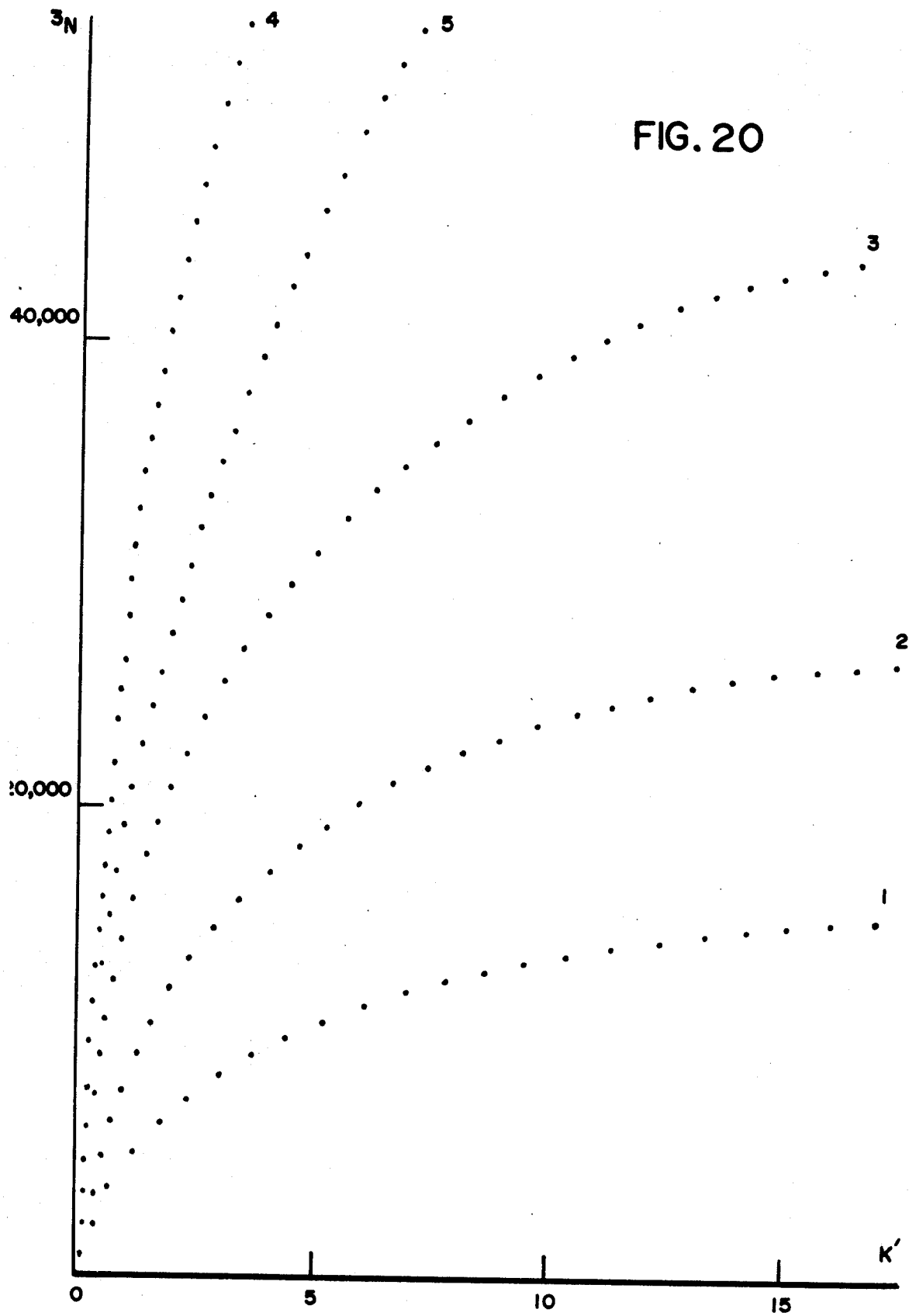
FIG. 20 is a plot of the peak capacity in three-dimensional column chromatography versis the value of k' at which the analysis is stopped.

FIG. 20—Plot of the peak capacity in $(CC)^3$ vs the value of k' at which the analysis is stopped. Columns are 10×10×10 cm. 1—$d_p=10$ μm; 2—$d_p=7$ μm; 3—$d_p=5$ μm; 4—$d_p=3$ μm. Curves 1-4, $A=1.0$; $C=0.03$. Curve 5—$d_p=5$ μm, $A=0.70$; $C=0.01$. Reduced velocity $v=14$.

We shall calculate the spot or peak capacity in two cases, in $(TCC)^2$ where development is stopped after one column volume has been pumped through the system successively in both directions and in $(CC)^2$ when one column volume is pumped through the system in the first direction and then elution is carried out in the second direction as in classical column chromatography. Calculations will also be made in the case of $(TCC)^3$ and $(CC)^3$.

Let $L_1$ and $L_2$ be the two dimensions of the column used, which does not need to be square, $H_1$ and $H_2$ the plate heights in the two directions, $\sigma_i$ the standard deviation of the sample spot (2,3), $n_1$ and $n_2$ the spot (or peak) capacities in the two directions, $2_n$ and $3_n$ the spot capacities we are looking for in two and three dimension analysis respectively. $H_1$ and $H_2$ will be very close to each other as the same particule size must be used to make the entire column, otherwise a systematic transcolumn variation of the flow velocity occurs, twists the spot trajectories and leads to poor results. The reduced plate heights $h_1$ and $h_2$ could be expected to be similar since in both directions we have assumed them to be constant, i.e. we have assumed that molecular diffusion and packing heterogeneity controls the plate height as in HPLC. As we work at optimum velocity, h for two very similar packings will be very close.

We shall use the law of variance addition to calculate the spot size after its migrations (see FIGS. 9–14). After the first development is over, a spot which has migrated a distance z becomes ovoid. Its variance in the axial direction is $$\sigma_{1,a}^2=\sigma_i^2+zH_1 \tag{1}$$

while in the radial direction, i.e. in the second direction it is:

$$\sigma_{1,r}^2=\sigma_i^2+2\gamma D_1 t_1 \tag{2}$$

where t, is the development time in the first direction. In equation 2 we neglect the contribution to lateral dispersion due to anastomosis or stream splitting, which is approximated by 0.15 $d_p z$. This contribution is small compared to the other two in the RHS of equation 2 at the flow velocities of interest in the present study.

During the second development or the elution along the second direction, the spot variance in the axial direction is:

$$\sigma_{2,a}^2=\sigma_i^2+2\gamma D_1 t_1+yH_2 \tag{3}$$

Since the initial variance of the spot, before migration in the second direction begins, is given by equation 2. This neglects the narrowing effect on a zone which enters a chromatographic bed in which it is retained, whose length is reduced in proportion to $R_f$.

Thus the spot capacity in $(TCC)^2$ will be somewhat underestimated, but not the peak capacity in $(CC)^2$ as the bands which leave the column are expanded at elution in the same ratio. Similarly the spot variance in the radial direction, i.e. the direction 1, becomes after the second elution:

$$\sigma_{2,r}^2=\sigma_i^2+zH_1+2\gamma D_2 t_2 \tag{4}$$

Since their variance at the beginning of their migration along the second direction was given by equation 1 and they expand radially by diffusion. In eq. 4 $t_2$ is the time of the second development.

The number of spots dn with resolution unity which can be placed along a distance dz on a chromatographic bed is given by:

$$dn = \frac{dz}{4\sigma} \tag{5}$$

while the number of peaks dn with resolution unity, eluted out of a column in a time dt is given by:

$$dn = \frac{dt}{4\sigma_t} = \frac{L}{4} \frac{dt}{t\sigma_e} \tag{6}$$

$\sigma_e$ and $\sigma_t$ are the zone standard deviation, in length and time unit respectively and t is the retention time, L(1+k')/u.

1°/Spot capacity in (TCC)²

At the end of the second development the spot standard deviations in the two directions are given by equations 3 and 4 respectively, hence:

$$d(^2n) = \frac{dz}{4\sigma_{2,r}} \frac{dy}{4\sigma_{2,a}} \tag{7}$$

The development times are respectively:

$$t_1 = \frac{L_1}{u_1} \tag{8a}$$

$$t_2 = \frac{L_2}{u_2} \tag{8b}$$

where $u_1$ and $u_2$ are the solvent velocities along the axis z and y respectively (see FIGS. 9–14).

Combination of equation 3,4 and 8 gives:

$$d^2n = \tag{9}$$

$$\frac{dy\,dz}{16\sqrt{\left(\sigma_i^2 + 2\gamma D_1 \frac{L_1}{u_1} + yH_2\right)\left(\sigma_i^2 + zH_1 + 2\gamma D_2 \frac{L_2}{u_2}\right)}}$$

Since $u_1$, $u_2$, $H_1$, $H_2$ are constants, integration of equation 9 is easy.

The integration limits are O and $L_1$ for z, O and $L_2$ for y. We obtain:

$$^2n = \frac{1}{4H_1H_2}\left(\sqrt{\sigma_i^2 + 2\gamma D_1 \frac{L_1}{u_1} + L_2H_2} - \sqrt{\sigma_i^2 + 2\gamma \frac{D_1L_1}{u_1}}\right)\left(\sqrt{\sigma_i^2 + L_1H_1 + 2\gamma D_2 \frac{L_2}{u_2}} - \sqrt{\sigma_i^2 + 2\gamma D_2 \frac{L_2}{u_2}}\right) \tag{10}$$

In the particular case where $\sigma_i$ is negligible and the plate characteristics in both directions (H,D,L,u) can be considered as equal, equation 10 simplifies to:

$$^2n = \frac{L}{4H^2}\left(\sqrt{2\gamma \frac{D}{u} + H} - \sqrt{\frac{2\gamma D}{u}}\right)^2 \tag{11}$$

Using the classical values of the reduced plate height and velocity $$h = \frac{H}{d_p} \tag{12a}$$

$$v = \frac{ud_p}{D_m} \tag{12b}$$

we obtain:

$$^2n = \frac{N}{4h}\left(\sqrt{h + \frac{2\gamma}{v}} - \sqrt{\frac{2\gamma}{v}}\right)^2 \tag{13}$$

At very large velocities i.e. negligible radial diffusion in both developments, the limit spot capacity would be N/4. But since N decreases with increasing solvent velocity thereis clearly an optimum. It is obtained by eliminating N from equation 13 and searching the value of $v$ which makes equal to 0 the derivative of $^2n$ by respect to $v$:

$$^2n = \frac{L}{4d_p} \frac{1}{h^2}\left(\sqrt{h + \frac{2\gamma}{v}} - \sqrt{\frac{2\gamma}{v}}\right)^2 \tag{14}$$

with:

$$h = \frac{2\gamma}{v} + Av^{\frac{1}{3}} + Cv \tag{15}$$

The solution is obtained by a numerical procedure.

In many cases a square plate will be used, with very similar properties in both directions, but the sample spot, will not have a negligibly small dimension. Then equation 10 simplifies to:

$$^2n = \frac{L}{4d_p} \frac{1}{h^2}\left(\sqrt{\frac{\sigma_i^2}{Ld_p} + \frac{2\gamma}{v} + h} - \sqrt{\frac{\sigma_i^2}{Ld_p} + \frac{2\gamma}{v}}\right)^2 \tag{16}$$

Equation 16 shows that the sample spot will not contribute markedly to a decrease of the plate performance as long as $\sigma_i^2$ is small compared to $Ld_p$.

2°/Spot capacity in (TLC)³

It is very easy to generalize equations 9–11 to the case of a three dimentional chromatographic medium. In the simple case when the characteristics of the three chromatographic systems used are the same and the sample spot is negligibly small we have the simplified equation:

$$^3n = \frac{L^{3/2}}{8H^3}\left(\sqrt{\frac{4\gamma D}{u} + h} - \sqrt{\frac{4\gamma D}{u}}\right)^3 \tag{17}$$

hence:

$$3n = \left(\frac{L}{d_p}\right)^{3/2} \frac{1}{8h^3} \left(\sqrt{h + \frac{4\gamma}{v}} - \sqrt{\frac{4\gamma}{v}}\right)^3 \quad (18)$$

The term $4\gamma/v$ instead of $2\gamma/v$ originates from the fact that now there are three successive developments and the spots enlarge by molecular diffusion in the two directions perpendicular to the direction of their migration.

Numerical calculations have to be made in order to determine the optimum velocity of the solvent.

3°/Peak capacity in (CC)$^2$

In this case the compounds are eluted out of the column by the second solvent, to be detected on-line, after a first separation has been made along the first dimension of the plate, as a development. At instant t there is a number:

$$n_1 = \int_0^{L_1} \frac{dz}{\sqrt[4]{\sigma_i^2 + zH_1 + 2\gamma D_2 t}} = \quad (19)$$

$$\frac{1}{2H_1}\left(\sqrt{\sigma_i^2 + L_1 H_1 + 2\gamma D_2 t} - \sqrt{\sigma_i^2 + 2\gamma D_2 t}\right)$$

of spots aligned along the exit edge of the plate. The time, t, during which they have undergone diffusion in the radial direction, i.e. the direction perpendicular to the elution (see FIGS. 9-14) increases during elution, hence their number decreases.

During a time dt, the number of spots eluted is given by an equation similar to equation 6, the time and length standard deviation being related by:

$$\sigma_e = \sigma_t \frac{L}{t}. \quad (20)$$

where $\sigma_e$ is the length standard deviation of the spot at column exit and is given by equation 3 with $y = L_2$. Accordingly:

$$d^2 n = n_1 dn_2 = \quad (21)$$

$$\frac{(\sqrt{\sigma_i^2 + L_1 H_1 + 2\gamma D_2 t} - \sqrt{\sigma_i^2 + 2\gamma D_2 t})L_2}{8H_1 \sqrt{\sigma_i^2 + 2\gamma D_1 t_1 + L_2 H_2}} \frac{dt}{t}$$

In equation 21, $t_1$ is the time of the first development, $L_1/u_1$, so if we assume that $D_1$ is approximatively the same for all compounds, we can define for the elution step a plate number:

$$N_2 = \frac{L_2}{\sigma_i^2 + 2\gamma D_1 t_1 + L_2 H_2} \quad (22)$$

similar to the column plate number but smaller because of the finite size of the spots at the end of the first development when elution is started.

Integration of equation 22 can be carried out using the relationship:

$$\int \frac{\sqrt{a+bt}}{t} dt = 2\sqrt{a+bt} + \sqrt{a} \ln \frac{\sqrt{a+bt} - \sqrt{a}}{\sqrt{a+bt} + \sqrt{a}} \quad (23)$$

The integration limits are $t_R$, the retention time at which the analysis is considered as finished, and $t_o$, the breakthrough time. They are related by the classical equation:

$$t_R = (1+k')t_o \quad (24)$$

Hence integration of equation 21 gives:

$$2n = \frac{\sqrt{N_2}}{8H_1}\left[2\sqrt{\sigma_i^2 + L_1 H_1 + 2\gamma D_2 t_R} - 2\sqrt{\sigma_i^2 + L_1 H_1 + 2\gamma D_2 t_o} - 2\sqrt{\sigma_i^2 + 2\gamma D_2 t_R} + 2\sqrt{\sigma_i^2 + 2\gamma D_2 t_o} + \right.$$

$$\sqrt{\sigma_i^2 + L_1 H_1} \ln \frac{(\sqrt{\sigma_i^2 + L_1 H_1 + 2\gamma D_2 t_R} - \sqrt{\sigma_i^2 + L_1 H_1})(\sqrt{\sigma_i^2 + L_1 H_1 + 2\gamma D_2 t_o} + \sqrt{\sigma_i^2 + L_1 H_1})}{(\sqrt{\sigma_i^2 + L_1 H_1 + 2\gamma D_2 t_R} + \sqrt{\sigma_i^2 + L_1 H_1})(\sqrt{\sigma_i^2 + L_1 H_1 + 2\gamma D_2 t_o} - \sqrt{\sigma_i^2 + L_1 H_1})} +$$

$$\left. \sigma_i \ln \frac{(\sqrt{\sigma_i^2 + 2\gamma D_2 t_R} + \sigma_i)(\sqrt{\sigma_i^2 + 2\gamma D_2 t_o} - \sigma_i)}{(\sqrt{\sigma_i^2 + 2\gamma D_2 t_R} - \sigma_i)(\sqrt{\sigma_i^2 + 2\gamma D_2 t_o} + \sigma_i)}\right] \quad (25)$$

Again if we can neglect $\sigma_i$, and consider that the plate characteristics are equal in the two directions, the equation 25 simplifies considerably, into:

$$2n = \frac{L}{4H}\left[\sqrt{1 + \frac{2\gamma(1+k')}{hv}} - \sqrt{1 + \frac{2\gamma}{hv}} - \sqrt{\frac{2\gamma(1+k')}{hv}} + \sqrt{\frac{2\gamma}{hv}} + \right. \quad (26)$$

$$\frac{1}{2} \text{Ln} \frac{\left(\sqrt{1 + \frac{2\gamma(1 + k')}{hv}} - 1\right)\left(\sqrt{1 + \frac{2\gamma}{hv}} + 1\right)}{\left(\sqrt{1 + \frac{2\gamma(1 + k')}{hv}} + 1\right)\left(\sqrt{1 + \frac{2\gamma}{hv}} - 1\right)} \cdot \frac{1}{\sqrt{1 + \frac{2\gamma}{v}}}$$

Even in this case the derivation of the optimum velocity is not straight forward and is best carried out by numerical calculations.

4°/Peak capacity in $(CC)^3$

The sample is placed at the corner of a face of a cube and the separation is first carried out as for $(TCC)^2$ by using two successive developments, parallel to the two edges of the cube; elution is then achieved along the third dimension. The number of spots spread over the exit face at time t is given by:

$$^2n = \int_o^{L_1} \int_o^{L_2} \frac{dy\, dz}{16\sqrt{\left(\sigma_i^2 + 2\gamma D_1 \frac{L_1}{u_1} + yH_2 + 2\gamma D_3 t\right)\left(\sigma_i^2 + zH_1 + 2\gamma D_2 \frac{L_2}{u_2} + 2\gamma D_3 t\right)}} \quad (27)$$

an equation similar to equation 9, where an additional term has been added to the lateral variances of the zone in the two directions perpendicular to the direction of elution, to account for radial diffusion during elution. Equation 27 is integrated in the same way than equation 9:

$$^2n = \frac{1}{4H_1H_2}\left(\sqrt{\sigma_i^2 + 2\gamma D_1 \frac{L_1}{u_1} + L_2H_2 + 2\gamma D_3 t} - \sqrt{\sigma_i^2 + 2\gamma D_1 \frac{L_1}{4_1} + 2\gamma D_z t}\right)\left(\sqrt{\sigma_i^2 + 2\gamma D_2 \frac{L_2}{u_2} + L_1H_1 + 2\gamma D_3 t} - \sqrt{\sigma_i^2 + 2\gamma \frac{D_2 L_2}{u_2} + 2\gamma D_3 t}\right) \quad (28)$$

The number of spots eluted out of the column during time dt is calculated by using an equation similar to equation 6 (cf.eqs. 19-21)=

$$d^3n = {}^2n\, dn = {}^2n \frac{L_3}{4\sigma_e} \frac{dt}{t} \quad (29)$$

where $^2n$ is given by equation 28 and is a function of time, while $\sigma_e$ is the standard deviation of the zones in the X axis (third direction) and is obtained by the law of variance addition:

$$\sigma_e^2 = \sigma_x^2 = \sigma_i^2 + 2\gamma D_1 \frac{L_1}{u_1} + 2\gamma D_2 \frac{L_2}{u_2} + L_3H_3 \quad (30)$$

If we assume that $D_1$ and $D_2$ are approximatively equal for all compounds, we can define a plate number for the elution step, $N_3$, defined exactly as $N_2$ (eq.22) except that we use now equation 30 for $\sigma_1^2$. Then:

$$^3n = \frac{\sqrt{N_3}}{16H_1H_2} \int_{t_o}^{t_R} \left(\sqrt{\sigma_i^2 + 2\gamma D_1 \frac{L_1}{u_1} + L_2H_2 + 2\gamma D_3 t} - \sqrt{\sigma_i^2 + 2\gamma D_1 \frac{L_1}{u_1} + 2\gamma D_3 t}\right) \quad (31)$$

$$\left(\sqrt{\sigma_i^2 + 2\gamma D_2 \frac{L_2}{u_2} + L_1H_1 + 2\gamma D_3 t} - \sqrt{\sigma_i^2 + 2\gamma D_2 \frac{L_2}{u_2} + 2\gamma D_3 t}\right) \frac{dt}{t}$$

Development of the integrand function gives four expressions similar to:

$$y = \frac{\sqrt{a + bt + ct^2}}{t} dt \quad (32)$$

whose integral is (32):

$$Y = \sqrt{a + bt + ct^2} + \frac{b}{2\sqrt{c}} \text{Ln}[2\sqrt{c(a + bt + ct^2)} + 2ct + b] - \sqrt{a}\, \text{Ln}\frac{2\sqrt{a(a + bt + ct^2)} + bt + 2a}{t} \quad (33)$$

for a positive. Identification with the corresponding terms of equation 31 permits its easy but tedious integration. There are four functions similar to Y in the integration of equation 31, the coefficients a, b, c being complex expressions of the parameters (for example $a_1 = (\sigma_i^2 + 2\gamma D_1(L_1/u_1) + L_2H_2)(\sigma_i^2 + L_1H_1 + 2\gamma D_2(L_2/u_2)$ and so on).

Since the technique of $(CC)^3$ is not very well understood yet and still far from the experimental stage it has not been found useful to print the complete equation at that stage. Calculations have been completed only in the simple case when $\sigma_i$ is negligible, the column is a cube and its properties identical in the three directions. The equation 33 simplifies to:

$$3_n = \frac{\sqrt{N_3}}{16H^2} \int_{t_o}^{t_R} \left( \sqrt{2\gamma \frac{DL}{u} + LH + 2\gamma Dt} - \sqrt{2\gamma \frac{DL}{u} + 2\gamma Dt} \right)^2 \frac{dt}{t} \quad (34)$$

In the development of the integrand function, only one expression such as equations 32-33 is found, with simple coefficients. Integration gives:

$$3_n = \frac{L^{3/2}}{16H^{3/2}\sqrt{1+2a}} \left[ 2ak' + \sqrt{8a(1+2a)} - \sqrt{4a(1+a+(1+2a)(1+k')+a(1+k')^2)} - \right. \quad (35)$$

$$(1+2a)\text{Ln} \frac{2\sqrt{a(1+a+(1+2a)(1+k')+a(1+k')^2)} + 2a(1+k') + 1 + 2a}{(1+k')[2\sqrt{2a(1+2a)} + 1 + 4a]} +$$

$$\left. \sqrt{4a(1+a)} \, \text{Ln} \frac{2\sqrt{(1+a)(1+a+(1+2a)(1+k')+a(1+k')^2)} + (1+2a)(1+k') + 2(1+a)}{(1+k')(2\sqrt{2(1+a)(1+2a)} + 3 + 4a)} \right]$$

with: $a = \frac{2\gamma}{hv}$ (35a)

a is always smaller than 1 (cf Equation 15); it is around 0.25 at optimum flow velocity and tends toward 0 when the velocity becomes very large.

For further calculations it is often useful to break H into $hd_p$, as h is also a function of the velocity, while the spot capacity is proportional to $(L/d_p)^{3/2}$. With such a complex expression there is no reason that the maximum spot capacity be obtained at the same velocity for different values of k'.

DISCUSSION

The simplified equations for spot or peak capacity of the various modes of chromatography discussed here are collected in Table I for easy further reference.

TABLE I

**Simplified* equations for column performance.**

$(TCC)^1 \quad n = \frac{1}{2}\sqrt{\frac{L}{H}}$ $(TCC)^2 \quad 2_n = \frac{L}{4 \cdot H}(\sqrt{1+a} - \sqrt{a})^2$ (14)

$(TCC)^3 \quad 3_n = \frac{1}{8}\left(\frac{L}{H}\right)^{3/2}[\sqrt{1+2a} - \sqrt{2a}]^3$ (18)

$(CC)^1 \quad n = \frac{1}{4}\sqrt{\frac{L}{H}}\text{Ln}(1+k')$ (38)

$(CC)^2 \quad 2_n = \frac{1}{8}\frac{L}{H}\frac{1}{\sqrt{1+a}}$ (26)

$$\left[ 2\sqrt{1+a(1+k')} - 2\sqrt{1+a} + 2\sqrt{a} - 2\sqrt{a(1+k')} + \text{Ln}\frac{(\sqrt{1+a}+1)(\sqrt{1+a(1+k')}-1)}{(\sqrt{1+a}-1)(\sqrt{1+a(1+k')}+1)} \right]$$

$(CC)^3 \quad 3_n = \frac{L^{3/2}}{16H^{3/2}\sqrt{1+2a}}$ (35)

$$\left[ 2ak' + \sqrt{8a(1+2a)} - \sqrt{4a(1+a+(1+2a)(1+k')+a(1+k')^2)} - \right.$$

$$(1+2a)\text{Ln}\frac{2\sqrt{a(1+a+(1+2a)(1+k')+a(1+k')^2)} + 2a(1+k') + 1 + 2a}{(1+k')[2\sqrt{2a(1+2a)} + 1 + 4a]} +$$

TABLE I-continued

Simplified* equations for column performance.

$$\sqrt{4a(1+a)} \; Ln \left[ \frac{2\sqrt{(1+a)(1+a+(1+2a)(1+k')+a(1+k')^2)} + (1+2a)(1+k') + 2(1+a)}{(1+k')(2\sqrt{2(1+a)(1+2a)} + 3 + 4a)} \right]$$

$a = \frac{2\gamma}{h\nu}$ $h = f(\nu)$ is given by the plate height equation.

*$\sigma_i = 0$. Column characteristics (L, D, u, h) identical in all directions.

Numerical calculations have been carried out in different cases, to investigate the effect of the various parameters of the four different experiments above, determine the range of performances which can be expected and find out reasonable values of the parameters permitting the achievement of high resolution separations while using a simple equipment with easy to meet specifications.

1°/Spot capacity in (TCC)$^2$

The spot capacity is given by either the general equation 10 or the simplified equation 14. It is easier to investigate first the simple case of a good square plate, developped at the same speed in the two directions, using retention mechanisms such that the diffusion coefficients in the two solvents are similar. The effect of deviations from this ideal case can be investigated.

For example with the typical values $\gamma = 0.7$; $A = 1$; $C = 0.03$, a numerical calculation shows that the maximum spot number (Equation 14) is achieved for $\nu = 8.9$, corresponding to $h = 2.50$. For a $10 \times 10$ cm column packed with $d_p = 5$ μm particules the maximum spot capacity is 1218, instead of 930 at the optimum flow velocity of 2.6 corresponding to the minimum plate height (1-99). The gain of 30% results from a trade-off between an increase in the axial variance and a marked decrease in the effect of lateral diffusion due to faster analysis.

For a typical value of the diffusion coefficient of $5 \times 10^{-6}$ cm$^2$/s the actual velocity corresponding to $\nu = 8.9$ is 0.089 cm/s (5 μm particules). The development time is 112 seconds in both directions, i.e. less than 4 minutes total, which is a drastic reduction compared to typical analysis time in TLC or even column chromatography: the chromatograph should be fully automatized to ensure reproducible results. The corresponding pressure for a solvent whose viscosity is 0.01 Poise would be:

$$\Delta P = (u\eta L/k_o d_p^2) = 35.6 \text{ atm} \tag{36}$$

Because of leak problems, especially on the side of the column, and the kind of safety problems which originate in an equipment designed as the one of Tyihak where the membrane would have to be applied on the $10 \times 10$ cm$^2$ column with a pressure exceeding 40 atm, generating a bursting force of more than 4 tons, first experiments will be made using coarser particles, lower velocities and less viscous solvents.

Equation 14 shows that with 10 μm particules and a reduced velocity 2.6, still a spot capacity exceeding 450 can be generated with a total analysis time of 26 minutes and a pressure of 2.6 atm. This would be very easy to achieve. Performances corresponding to other combinations of parameters are given in Table II where it is seen that extremely large spot capacities can be produced in reasonable times and that the most critical problem is the design of the mechanical enclosure to contain the pressure. A spot capacity of 1,000 could be approached with a pressure drop of 10 atm.

TABLE II

Performances of (TCC)$^n$ columns.

| $d_p$(μm) | $\nu^d$ | $^1n^a$ | $^2n^a$ | $^3n^a$ | $t^c$(min) | $\Delta P^b$(atm) |
|---|---|---|---|---|---|---|
| 3 | 12.6 | 54 | 1960 | 70050 | 0.80 | 233 |
|   | 8.9 | 58 | 2030 | 67900 | 1.12 | 165 |
|   | 5.7 | 61 | 1960 | 59200 | 1.77 | 105 |
|   | 2.6 | 65 | 1540 | 35000 | 3.85 | 48 |
| 5 | 12.6 | 42 | 1170 | 32500 | 1.33 | 50 |
|   | 8.9 | 45 | 1218$^e$ | 31600 | 1.87 | 36 |
|   | 5.7 | 47 | 1177 | 27500 | 2.93 | 23 |
|   | 2.6 | 50 | 923$^e$ | 16280 | 6.4 | 10.4 |
| 7 | 12.6 | 35 | 840 | 19650 | 1.87 | 18.4 |
|   | 8.9 | 38 | 870 | 19050 | 2.62 | 13 |
|   | 5.7 | 40 | 841 | 16600 | 4.1 | 8.3 |
|   | 2.6 | 42 | 660 | 9830 | 9.0 | 3.8 |
| 10 | 12.6 | 29 | 588 | 11510 | 2.6 | 6.3 |
|    | 8.9 | 32 | 609$^e$ | 11150 | 3.75 | 4.5 |
|    | 5.7 | 33 | 589 | 9720 | 5.83 | 2.8 |
|    | 2.6 | 36 | 462 | 5760 | 12.8 | 1.3 |
| 15 | 12.6 | 24 | 392 | 6260 | 4.0 | 1.9 |
|    | 8.9 | 26 | 406 | 6070 | 5.6 | 1.3 |
|    | 5.7 | 27 | 392 | 5300 | 8.8 | 0.84 |
|    | 2.6 | 29 | 308 | 3130 | 19. | 0.4 |

$^a$ $^1n$, $^2n$, $^3n$ spot capacities of (TCC)$^1$, (TCC)$^2$ and (TCC)$^3$ columns respectively. Columns characteristics are the same in all dimensions (L = 10 cm; $\gamma$ = 0.70; A = 1.0; C = 0.03)
$^b$ [$\Delta P$ is the pressure drop necessary to pump the solvent at the reduced velocity indicated, with $D_m = 5 \times 10^{-6}$ cm/s; $\eta$ = 1cP; permeability is $d_p^2/1000$.
$^c$ [t is the retention time of an inert compound, $t_o$ or breakthrough time. Analysis time is nt (n number of dimensions of the column) plus time necessary for intermediate steps like drying...
$^d$ [column efficiency: $\nu$ = 2.6, h = 1.99(minimum); $\nu$ = 5.7, h = 2.20; $\nu$ = 8.9, h = 2.50; $\nu$ = 12.6, h = 2.82.
$^e$ The number underlined correspond to curves 1-3 on FIG. 15.

FIG. 15 shows the variation of $^2n$ with increasing sample standard deviation as predicted by equation 16. A rather small sample spot is an important requirement. The specifications are more drastic than in conventional TLC since the performances are better, i.e. the final spots are smaller. These specifications are comparable to those encountered in column chromatography.

As a first approximation we can require:

$$\sigma_i^2 < 0.1 L d_p \tag{37}$$

which leads to reasonable results (FIG. 15). The reduction in spot capacity is then 10-15%. When $\sigma_i^2/Ld_p$ becomes large, the spot capacity is markedly reduced and eventually tends towards zero. A limited development of the RHS of equation 16 for small values of $Ld_p/\sigma_i^2$ shows that $^2n$ becomes equivalent to $L^2/16\sigma_i^2$. This upper limit of spot capacity is shown on FIG. 15.

As it has been shown that it is quite possible to apply TLC samples with standard deviation around 0.3 mm and to inject samples in CC which are small enough not to contribute significantly to band broadening, there should not be major unexpected difficulties in meeting those specifications and achieving large spot capacities.

Equations 14 and 16 show that the spot capacity depends essentially on the column dimension (L), the particule size ($d_p$) and the reduced plate performances (h,ν), exactly the characteristics which determine the peak capacity of a conventional column. From previous discussions on optimization of column performances we know what to do to increase the spot capacity in (TCC)[2]: the packing homogeneity will be critical. For example with h=4 at a reduced velocity of 8 the spot capacity of a 10×10 cm plate made with 5 μm particules is only 825 instead of 1218 if h=2.50. The diffusion coefficient has no effect on the spot capacity, only on the analysis time and pressure.

2°/Spot capacity in (TCC)[3]

Some numerical calculations have been made with the same conditions as above. The optimum velocity is still larger than in (TCC)[2] since it is useful to decrease the time during which the spots broaden through lateral diffusion. In the case selected (A=1; C=0.03) the optimum velocity is now 12.6 (cf Table II).

The spot capacity becomes extremely large with values exceeding markedly $1 \times 10^4$ within easy reach, while 100,000 does not seem impossible to reach anymore.

The critical problems in this case are first column packing, as we can foresee the packing problems associated with the manufacturing of a 10×10×10 cm or larger cube, and then to find out a suitable detector: it does not appear practical to slice the cube in 0.1 mm thick cuts and scan one by one the 1,000 slices with a photodensitometer.

The potential reward appears worth of serious research investment in this area, however.

3°/Peak capacity in (CC)[2]

At a later stage it will probably be necessary to investigate rectangular plates, especially when the two retention mechanisms used will have markedly different selectivity for the components of a complex mixture and optimization will be complex as the two dimensions of the plate and the order in which the two separation mechanisms will be applied may have significant effect on the overall performance. At that stage it is sufficient, however, to consider square columns and assume that their performances are the same in both directions. In fact what is n t most probably the largest difference in properties in the two dimensions is the diffusion coefficient of the solutes in the mobile phase and its viscosity. These parameters determine the analysis time and the pressure drop but have little influence on the spot capacity provided the same reduced velocity is chosen.

The effect of the size of the original sample spot have not been taken into account in this study either: the specifications will be similar in (TCC)[2] and (CC)[2] and we have already calculated them and seen that they can be satisfied with a careful instrument design: keeping $\sigma_r^2/Ld_p$ smaller than 0.1 will result in a loss in peak capacity not exceeding about 10%.

It is seen in equation 26 that the peak capacity depends separately on the ratio of column length to particule size, on the range of k' scanned during elution and on the column bed performance, i.e. the reduced plate height at the value of reduced velocity at which the column is operated. The influence of these three factors can be studied separately.

The peak capacity increases steadily with increasing range of k' (FIG. 16). We know that in CC the time optimum range is 0-6.4: the largest peak capacity in a given time, $t_A$, is obtained by adjusting column length and solvent strength so that the compound with k'=6.4 is eluted at time $t_A(1)$. This is because the peak capacity in CC is given by:

$$n = \frac{\sqrt{N}}{4} \text{Ln}(1 + k') \qquad (38)$$

and that selecting k'=6.4[$Ln(1+k')$=2] achieves the best compromise between the effect on analysis time of an increase in column length and k'-range scanned. Equation 26 is much more complicated than equation 38 and it is not possible to obtain a general result in (CC)[2].

Nevertheless we have chose the value k'=7 as the end of the analysis when such a choice is necessary, in the following discussion. The dotted line on FIG. 4 shows the variation of the peak capacity of a column (Equation 38) having 4 million theoretical plates, for sake of comparison. The curve appears steeper than those corresponding to (CC)[2], which saturate faster. Consequently is would probably not be worth while to continue development after k'=5 or so in (CC)[2], if we could optimize the plate dimensions and solvent compositions. On the other hand if 1200 spots are eluted out of the column (A=1) between k'=0 and k'=5, still 300 are eluted between k'=5 and k'=10 and that capacity could appear useful when it is difficult to increase the size of the (CC)[2] equipment. This explains why the value k'=7 is assumed to be a good comparison. Furthermore if we compare equations 14 and 26 (Table II) we see that the value of k' at which the spot capacity of (TCC)[2] is equal to the peak capacity of (CC)[2] depend only on a, and thus on the plate height coefficients. With the numerical values selected here (A=1.0; C=0.03), we obtain the same resolution power for k'=6.5, a value very close that for which peak capacity of a conventional column is equal to the spot capacity of an overpressured TLC plate (k'=6.4).

The peak capacity is a function of the plate characteristics which determine both a=2γ/hν and h. There is of course no reason that the maximum peak capacity be achieved for the velocity which gives the minimum plate height: a faster velocity results in a larger variance contribution in the direction of the solvent migration but, because residence time is smaller, in a smaller variance contribution in the perpendicular direction.

FIG. 17 shows that there is an optimum velocity markedly larger than the one corresponding to the minimum plate height, as in (TCC)[2], as discussed in Table II. This optimum velocity increases slightly with the range of k' scanned during the analysis and in the conditions of the figure is around ν=6.5. The peak capacity is almost 20% larger than at $ν_o$=2.6. We note in passing that these results are independent of the plate size and particule diameter. The peak capacity is merely proportional to the length of the column side and inversely proportional to dp. On the other hand the results shown on FIG. 17 depend on the values of γ, A and C in equation 15. There is little we can do about γ(28,29). A depends on the homogeneity of the bed packing and for a thin layer bed it should not be too difficult to obtain values of A smaller than 1. C describes the mass transfer in the particule and is certainly a function of k' but as a first approximation can be assumed to be constant.

FIG. 1B shows the variation of the peak capacity with the constants A and C, for a 10×10 cm column packed with 5 μm particles, values well in excess of 1500 can be expected at k'=7. The reduced velocity is 7, corresponding to the maximum peak capacity for $A=1$, $C=0.03$, but certainly not for the other values of these parameters. It can be expected to increase slowly with decreasing values of A and C.

Accordingly we can expect to be able to generate a peak capacity close to 1000 by using a $10 \times 10$ cm column, packed carefully $A=0.7$ with 10 μm particles as typically used in CC, with a reduced velocity close to 7, a pressure drop around 5 atm (Table II) and recording the chromatograph for values of k' up to ca 10.

4°/Peak capacity in (CC)³

In view of the difficulties encountered in the design and construction of a (CC)² chromatograph it seems too early to discuss in details the potential performances of a (CC)³ chromatograph. Furthermore equation 35 is similar to equation 26, the parameters L and $d_p$ are separated from the column characteristics and the consequences will be similar to those encountered in (CC)². The numbers, however, are now gigantic.

The peak capacity is maximum for a relatively large value of the reduced velocity, which would be quite convenient for the analysis of heavy molecular weight compounds such as biopolymers. The optimum reduced velocity is around 14, but would be markedly smaller should the performance of the three dimensional packed bed be less satisfactory than assumed in the calculations (FIG. 19).

The peak capacity increases very rapidly with increasing k' at the beginning, but levels off at values above 10. It is clear from equation 35 that there is a limit at large k'. A peak capacity equal to the spot capacity of the same column used in (TCC)³ is achieved for $k'=6.8$ with the numerical values chosen here ($A=1.0$; $C=0.03$). The limit at very large k' is about 50% larger so in practice it is not easy to have better separation efficiency in (CC)³ than in (TCC)³.

The peak capacity increases very rapidly with increasing ratio of column length to particle size (cf FIG. 8). As in (TCC)³, peak capacities of several ten thousands would be easy to reach while a capacity of 100,000 is a theoretical possibility, for example with a $12 \times 12 \times 12$ cm cube well packed with 3 μm particles!

The potential performances of mono-, bi-, and tridimensional column chromatography are compared in Table III. It must be understood that the peak capacities are not obtained at the same reduced velocity so the ratio $^2n/n$ and $^3n/^2n$ have been calculated just to show that the peak capacity increases more slowly than with the power of the space dimension used.

TABLE III

Comparison between the performances of CC, (CC)² and (CC)³ column*

| k' | $^1n$ | $^2n$ | $^2n/^1n$ | $^3n$ | $^3n/^2n$ |
|---|---|---|---|---|---|
| 1 | 17 | 500 | 29 | 13400 | 27 |
| 3 | 34 | 950 | 27 | 25000 | 26 |
| 5 | 44 | 1180 | 26 | 30800 | 26 |
| 7 | 52 | 1320 | 25 | 34400 | 26 |
| 10 | 60 | 1470 | 24 | 37900 | 26 |
| 20 | 76 | 1720 | 23 | 38500 | 22 |

*$L = 10$ cm; $d_p = 5$ μm $A = 1.0$, $C = 0.03$, $\gamma = 0.70$ CC is operated at $\nu = 2.6$, (CC)² at $\nu = 7$ and (CC)³ et $\nu = 14$ h is respectively: 1.99; 2.32 and 2.93.

Thus we have provided a multi-column real-time chromatograph in which a plurality of samples may be injected into a flowing sheet of fluid to be eluted out across a linear detector (MTCC). We have provided a two-dimensional liquid chromatograph in which overpressure development is provided in both directions. If development in the second direction is stopped before elution of the desired components, the chromatogram may be read in a conventional manner (TCC)². If elution is continued the components are detected as they pass by a linear array detector (CC)². We have provided three-dimensional column chromatograph (CC)³. We have provided novel apparatus for peforming the above, including a steel cuvette for performing (MTCC), (TCC)² and (CC)², a block separation medium and tomagraphic detector for providing a third separation after (CC)² and have derived criteria for selecting optimum flow rates during separation.

It will thus be seen that the objects set forth above, among those made apparent from the preceding description, are efficiently attained and, since certain changes may be made in carrying out the above methods and systems and in the constructions set forth without departing from the scope of the invention, it is intended that all matter contained in the above description or shown in the accompanying drawing shall be interpreted as illustrative and not in a limiting sense.

Particularly, although we have discussed the first chromatographic development as producing a linear array of sub-components and the second dimensional chromatographic development as producing a planar array of sub sub-components, it will be understood by those skilled in the art that the first development is uni-dimensional and may be along a curve as well as a straight line, and the second development is two-dimensional and may be on a curved surface as well as a flat surface. Where we have described the use of multiple photo diode detectors, scanning detectors using flying spots, or cathode ray devices may also be employed. In fact any form of detector suitable to measure the quality of an unknown component being sought may be employed, such as electro-chemical detectors.

Where we have mentioned two or three retention media, it will be understood that the stationary phase may be the same in successive dimensional developments and the fluid phase changed, or vice versa, or the fluid and stationary phases may be different in each separate development. Other separation mechanisms known in the art may be employed such as absorption chromatography in normal or reverse phase or electrophoresis.

It is also to be understood that the following claims are intended to cover all of the generic and specific features of the invention herein described and all statements of the scope of the invention which, as a matter of language, might be said to fall therebetween.

Having described our invention, what we claim as new and desire to secure by Letters Patent is:

1. A method of multi-dimensional chromatography comprising:
    (A) chromatograpically separating an unknown into an array of constituents in a chromatographic bed;
    (B) chromatographically separating said constituents into a second array of sub-constituents in a closed vessel by pumping a fluid through said bed in a direction crossing said array; and
    (C) detecting said sub-constituents as they flow past fixed positions in said second direction.

2. A method of three-dimensional chromatography comprising:
    (A) chromatographically separating an unknown into a one-dimensional array of constituents;

(B) chromatographically separating said constituents into a second two-dimensional array of sub-constituents in a chromatographic bed;
(C) chromatographically separating said sub-constituents in a closed vessel into a three-dimensional array of sub sub-constituents by pumping a fluid through said bed in a direction crossing said two-dimensional array; and
(D) detecting said sub sub-constituents as they flow past fixed positions in said crossing direction.

3. The method of claims 1 or 2 wherein said first step is accomplished by pumping a fluid through a two-dimensional column of a chromatographic bed and then injecting an unknown into the flowing column.

4. The method of claim 3 wherein one or more chromatographic separating steps, but not the last, is accomplished by means of electrophoresis.

5. The method of claim 3 wherein said crossing direction is orthogonal to said array.

6. A multi-dimensional chromatographic system comprising:
(A) first means for chromatographically separating components of an unknown into an array of components;
(B) second means for further separating said components in a closed vessel into a higher dimensional array of components by pumping a fluid through said first array of components; and
(C) third means for detecting the time of transit and concentration of said components as they pass fixed positions spaced away from the initial array position.

7. A multi-dimensional chromatographic system comprising:
(A) a two-dimensional chromatographic column having an entrance edge and an outlet edge and a thin sheet-like stationary phase therebetween;
(B) first means for chromatographically separating components of an unknown to cause them to be linearly disposed along said entrance edge of said column;
(C) second means for pumping a fluid through said column in a direction across said linearly disposed components; and
(D) third means for detecting the time at which said components exit said column and their concentration.

8. The system of claims 6 or 7 wherein said first means comprises
(a) means for pumping a fluid, and
(b) means for introducing a sample into the flowing fluid.

9. The system of claim 8 wherein said second means pumps said fluid in a direction orthogonal to said first means.

10. A chromatographic plate for multi-dimensional chromatography comprising:
(A) a flat plate;
(B) a first area adjacent the edge of said plate on a side of said plate covered with a layer of a first chromatographic retention medium;
(C) a second area adjacent said first area on said side of said plate covered with a layer of a second chromatographic retention medium; and
(D) a third area adjacent said second area on said side of said plate not being optically obscured.

11. A chromatographic plate for multi-dimensional chromatography comprising:
(A) a flat plate;
(B) a first area adjacent the edge of said plate on a side of said plate covered with a layer of a first chromatographic retention medium; and
(C) a second area adjacent said first area on said side of said plate being free of said chromatographic retention medium.

12. A chromatographic unknown component separation system comprising:
(A) a two-dimensional chromatographic column having an entrance edge at which a plurality unknowns may be introduced and an outlet edge and a thin sheet-like stationary phase therebetween;
(B) first means for pumping fluid through said column across said entrance edge; and
(C) second means for detecting the time at which components arrive at said outlet edge and their concentration.

13. The system of claim 12, and
(D) means for introducing one or more unknowns into the flowing fluid.

14. The system of claim 13 wherein said introducing means provides for introducing said unknowns along said entrance edge.

15. The system of claims 12, 13, or 14 wherein said first means pumps said fluid in a direction orthogonal to said entrance edge.

16. The method of chromatographically separating components of a sample by
(A) first pumping a fluid in a thin sheet through a chromatographic separating medium;
(B) then introducing a sample into the flowing sheet; and
(C) then detecting said components as they flow by in said flowing sheet.

17. A chromatographic system comprising:
(A) means for pumping a fluid in a thin sheet through a chromatographic separating medium;
(B) means for introducing a sample into the flowing sheet; and
(C) means for detecting said components as they flow by in said flowing sheet.

18. The method or system of claims 16 or 17 wherein many samples are introduced into the flowing sheet in an array across said flowing sheet.

19. The method of claim 18 wherein the flow rate of said flowing sheet is substantially the optimum flow rate for maximum separation efficiency.

20. The method of chromatographically separating components of a sample comprising:
(A) over-pressure development of a sample into a first one-dimensional array of components; and
(B) over-pressure development of said first array into a second two-dimensional array.

21. The method of claim 20 and
(C) reading said developed two-dimensional chromatogram.

22. Chromatographic apparatus comprising:
(A) a cuvette plate having
(a) a central cavity in the form of a parallelogram, and
(b) first and second pairs of parallel grooves, each pair located on gravity sides of said cavity and parallel to the edges of said cavity;
(B) a cover plate having
(a) a central cavity of smaller area than and located over said central cavity in said cuvette plate, (b) four grooves of larger area and each located over one of said grooves in said cuvette plate;

(C) a thin sheet of pliable material between said plates and separating their respective cavities and grooves;

(d) means for selectively supplying a solvent under pressure to one of the grooves of said first pair of grooves; and, (E) means for selectively supplying a solvent under pressure to one of the grooves of said second pair of grooves.

23. The chromatographic apparatus of claim 22 and (F) means for selectively supplying fluid under pressure to said cavity and grooves in said cover plate.

24. The chromatographic apparatus of claims 22 or 23

(G) means for applying vacuum to the grooves in said cover plate over each of said pair of grooves in said cuvette plate.

25. The chromatographic apparatus of claims 22 or 23 and (G) means for applying vacuum to the grooves in said cover plate over each of said pair of grooves in said cuvette plate.

26. The chromatographic apparatus of claims 22 or 23

(G) a channel for one of said grooves in said cuvette plate provide continued sheet-like flow therefrom, and (H) windows at both ends of a portion of said sheet-like flow such that light may pass through in the direction of said flow.

27. That which is claimed in claims 1, 2, 6, 7, 12, 16, 17, or 20 wherein the flow rate of said fluid is substantially the optimum flow rate for maximum separation efficiency.

28. A multi-dimensional chromatographic system comprising:

(A) first means for chromatographically separating components of an unknown into a two-dimensional array of components;

(B) second means for overpressured fluid chromatography comprising a vessel for enclosing said components for further separating said components into a higher dimensional array of components by forcing a fluid through said first array of components and through a solid block retention medium; and (C) third means for detecting the time of transit and concentration of said components as they pass fixed positions spaced away from the initial position array.

29. The multi-dimensional chromatographic system of claim 28 wherein said first means comprises a thin layer chromatographic plate.

30. The system defined in claims 6, 7, or 28 and (E) a chromatographic plate on which said chromatographic separation is accomplished comprising:

(a) a flat plate;

(b) a first area adjacent the edge of said plate on a side of said plate covered with a layer of a first chromatographic retention medium;

(c) a second area adjacent said first area on said side of said plate covered with a layer of a second chromatographic retention medium; and, (d) a third area adjacent said second area on said side of said plate not being optically obscured.

31. The system defined in claim 30 wherein said first area of said chromatographic plate is a rectangular strip, said second area is a larger rectangle and said third area is a rectangular strip.

32. The system defined in claim 31 wherein said chromatographic plate comprises a glass plate.

33. The chromatographic plate defined in claim 10 wherein said first area is a rectangular strip, said second area is a larger rectangular and said third area is a rectangular strip.

34. The chromatographic plate defined in claims 10 or 33 wherein said plate is glass.

35. The chromatographic plate defined in claims 10 or 33 wherein said plate is of porous material.

36. A chromatographic unknown component separation system comprising:

(A) a two-dimensional chromatographic column having an entrance at which a plurality of unknowns may be introduced and an outlet edge and a thin sheet-like stationary phase therebetween;

(B) means for forcing fluid through said column in a direction orthagonal to said entrance edge; and (C) means for detecting the time at which components arrive at said outlet edge.

* * * * *